(12) United States Patent
Suzuki et al.

(10) Patent No.: US 10,494,390 B2
(45) Date of Patent: Dec. 3, 2019

(54) ORGANIC MAGNESIUM PHOSPHIDE AND MANUFACTURING METHOD THEREOF, ORGANIC MAGNESIUM PHOSPHIDE COMPLEX AND MANUFACTURING METHOD THEREOF, AND MANUFACTURING METHOD OF ORGANIC PHOSPHORUS COMPOUND USING SAID PHOSPHIDE

(71) Applicant: HOKKO CHEMICAL INDUSTRY CO., LTD., Chuo-ku, Tokyo (JP)

(72) Inventors: Kenta Suzuki, Atsugi (JP); Nobumichi Kumamoto, Atsugi (JP); Nobuhiro Ito, Atsugi (JP); Shinji Hatae, Atsugi (JP); Hiroyuki Suzuki, Atsugi (JP)

(73) Assignee: HOKKO CHEMICAL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 16/314,342

(22) PCT Filed: Jun. 29, 2017

(86) PCT No.: PCT/JP2017/023925
§ 371 (c)(1),
(2) Date: Dec. 28, 2018

(87) PCT Pub. No.: WO2018/008510
PCT Pub. Date: Jan. 11, 2018

(65) Prior Publication Data
US 2019/0248815 A1   Aug. 15, 2019

(30) Foreign Application Priority Data

Jul. 4, 2016   (JP) ................. 2016-132831

(51) Int. Cl.
*C07F 9/50* (2006.01)
*C07B 49/00* (2006.01)
*C07F 3/02* (2006.01)

(52) U.S. Cl.
CPC ............ *C07F 9/5045* (2013.01); *C07B 49/00* (2013.01); *C07F 3/02* (2013.01); *C07F 9/5022* (2013.01); *C07F 9/50* (2013.01)

(58) Field of Classification Search
CPC ........ C07F 9/5045; C07F 9/5022; C07F 3/02; C07F 9/50; C07B 49/00
See application file for complete search history.

(56) References Cited

U.S. PATENT DOCUMENTS 4,101,587 A * 7/1978 Moedritzer ........... C07F 9/5407
568/11
4,412,979 A * 11/1983 Horn ....................... C01B 25/08
423/299
4,879,416 A   11/1989 Puckette et al.

FOREIGN PATENT DOCUMENTS

| CN | 102010442 A | 4/2011 |
| JP | H0774226 A | 3/1995 |
| WO | 9006930 A1 | 6/1990 |
| WO | 9947528 A1 | 9/1999 |

OTHER PUBLICATIONS

Castillo M. et al., Solid-Phase Organic Synthesis of Sensing Sorbent Materials for Copper and Lead Recovery, Journal of the Brazilian Chemical Society, 2005, vol. 16, No. 3A, p. 412-417.
Damian et al., Palladium-catalysed P-C bond forming reactions between diphenylphosphine and ortho-substituted aryl bromides, Applied Organometallic Chemistry, 2009, vol. 23, pp. 272-276.
Day, B.M. et al., Synthesis and Reactivity of the Phospha-Grignard Reagent Mg (P{SiMe3}2) Br(thf), European Journal of Inorganic Chemistry, 2010, vol. 2010, No. 34, p. 5471-5477.
International Search Report (ISR) dated Aug. 22, 2017, issued for International application No. PCT/JP2017/023925.

(Continued)

*Primary Examiner* — Rosalynd A Keys
(74) *Attorney, Agent, or Firm* — Law Office of Katsuhiro Arai

(57) ABSTRACT

An organic magnesium phosphide expressed by Formula (1) below and an organic magnesium phosphide complex expressed by Formula (9) below are provided, and a manufacturing method of organic phosphorus compound is characterized in that the above compounds used as a reagent is reacted with an electrophile:

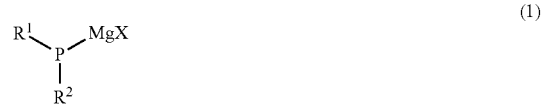

wherein $R^1$ and $R^2$ are each independently an aliphatic group, heteroaliphatic group, alicyclic group, or heterocyclic group, and X is chlorine, bromine, or iodine,

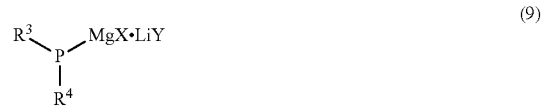

wherein $R^3$ and $R^4$ are each independently an aliphatic group, heteroaliphatic group, aromatic group, alicyclic group, or heterocyclic group, and X and Y are each independently chlorine, bromine, or iodine.

14 Claims, No Drawings

(56) References Cited

OTHER PUBLICATIONS

Ren, H. et al., Stereoselective Preparation of Functionalized Acyclic Alkenylmagnesium Reagents Using i-PrMgCl•LiCl, Organic Letters, 2004, vol. 6, No. 23, p. 4215-4217.
Xin-Min et al., Synthesis and Coordination Properties of New Bis(phosphinomethyl)pyridine N,P,P'-Trioxides, Inorganic Chemistry, 2001, vol. 40, pp. 4420-4427.
Notification Concerning Transmittal of International Preliminary Report on Patentability (PCT/IB326) and Notification of Transmittal of Translation of the International Preliminary Report on Patentability (PCT/IB/338) dated Jan. 17, 2019, with International Preliminary Report on Patentability (PCT/IB/373) and Written Opinion of the International Searching Authority (PCT/ISA/237), for corresponding international application PCT/JP2017/023925, (13 pages).

\* cited by examiner

ORGANIC MAGNESIUM PHOSPHIDE AND MANUFACTURING METHOD THEREOF, ORGANIC MAGNESIUM PHOSPHIDE COMPLEX AND MANUFACTURING METHOD THEREOF, AND MANUFACTURING METHOD OF ORGANIC PHOSPHORUS COMPOUND USING SAID PHOSPHIDE

CROSS-REFERENCE TO RELATED APPLICTIONS

This application is the U.S. National Phase 35 U.S.C. § 371 of International Application PCT/JP2017/023925, filed Jun. 29, 2017, which claims priority to Japanese Patent Application No. 2016-132831, filed Jul. 4, 2016. The International Application was published under PCT Article 21(2) in a language other than English.

TECHNICAL FIELD

The present invention relates to: a new organic magnesium phosphide characterized by phosphorus-magnesium bond and a manufacturing method thereof; a new organic magnesium phosphide complex and a manufacturing method thereof; and a new manufacturing method of organic phosphorus compound using such organic magnesium phosphide or organic magnesium phosphide complex.

BACKGROUND ART

Organic phosphorus compounds are used in wide-ranging applications such as ligands in transition metal catalysts and hardening accelerators for epoxy resins. For example, an organic phosphorus compound expressed as 1,2-bis (di-t-butyl phosphinomethyl) benzene is a catalyst ligand that exhibits highly desirable activity in the carbonylation reaction of olefinic unsaturated compounds. Also, an organic phosphorus compound expressed as 2,2'-bis diphenyl phosphanylmethyl-1,1'-biphenyl and derivatives thereof are catalyst ligands that exhibit highly desirable activity and selectivity in the hydroformylation reaction.

Among the key methods for manufacturing such organic phosphorus compounds, methods involving the reaction between a phosphinous chloride and a lithium reagent or Grignard reagent are well known (Patent Literature 1). Also, manufacturing methods using the reaction between a metal phosphide, one representative of which is lithium phosphide, and an electrophile, are also reported (Patent Literatures 2 to 5). However, these methods are not advantageous propositions in industrial applications because preparation of lithium phosphides requires highly hazardous metal lithium and expensive lithium reagents.

Metal phosphides also include synthesized magnesium phosphides, but their examples reported so far are limited to magnesium phosphides containing aromatic groups, such as $Ph_2PMgBr$ and PhOcPMgCl (Oc represents an octyl group) (Non-patent Literatures 1, 2). This is because preparing dialkyl magnesium phosphides having primary and secondary straight-chain alkyl groups as substituents is difficult, as the produced dialkyl magnesium phosphide reacts with the dialkyl phosphinous chloride used as a material, which explains why no example of synthesized dialkyl magnesium phosphide, where the phosphorus atom has two substituent alkyl groups, has been reported. Consequently, no manufacturing method of dialkyl phosphine compound has been reported which involves the reaction between a dialkyl magnesium phosphide and an electrophile.

On the other hand, dialkyl or trialkyl phosphine compounds having secondary or tertiary alkyl groups are particularly useful as ligands in transition metal catalysts for cross-coupling reactions, and such compounds of various structures have been proposed. These dialkyl or trialkyl phosphine compounds are generally manufactured by causing a dialkyl phosphinous chloride to react with an organic lithium reagent or Grignard reagent prepared from a halogen compound. There are problems, however, because preparing Grignard reagents from such halogen compounds as benzyl chloride, allyl chloride and cinnamyl chloride is difficult and requires special equipment, while preparation of lithium reagents from halogen compounds requires use of intermediates that contain heavy metals.

BACKGROUND ART LITERATURE

Patent Literature

Patent Literature 1: International Patent Laid-open No. WO99/47528
Patent Literature 2: U.S. Pat. No. 4,879,416
Patent Literature 3: International Patent Laid-open No. WO90/06930
Patent Literature 4: Chinese Patent No. 102010442
Patent Literature 5: Examined Japanese Patent Laid-open No. Hei 7-74226

Non-Patent Literature

Non-patent Literature 1: Applied Organometallic Chemistry, 2009, Vol. 23, pp. 272-276.
Non-patent Literature 2: Inorganic Chemistry, 2001, Vol. 40, pp. 4420-4427.

SUMMARY OF THE INVENTION

Problems to Be Solved by the Invention

The present invention was developed against the background explained above, and its object is to provide a new organic magnesium phosphide useful in the synthesis of organic phosphorus compounds and a manufacturing method of such organic magnesium phosphide, as well as a new organic magnesium phosphide complex and a manufacturing method of such organic magnesium phosphide complex.

Another object of the present invention is to provide a new manufacturing method of organic phosphorus compound using such organic magnesium phosphide or organic magnesium phosphide complex.

Means for Solving the Problems

After studying in earnest to solve the aforementioned problems, the inventors of the present invention found that, first and foremost, organic magnesium phosphides or organic magnesium phosphide complexes having primary or secondary straight-chain alkyl groups or other hydrocarbon groups, aromatic groups, etc., as substituents, can be prepared using the phosphorus-hydrogen bond exchange reaction between a Grignard reagent, or an organic magnesium complex to which lithium halide has been added, and a phosphine.

The inventors also found that, when preparing a magnesium phosphide from metal magnesium, adding a lithium halide allows a magnesium phosphide complex to be prepared much more efficiently, and it also produces the reaction liquid as a solution so that the obtained magnesium phosphide complex can be manipulated easily, instead of a slurry that makes such manipulation cumbersome.

Furthermore, the inventors discovered a new manufacturing method for synthesizing an organic phosphorus compound using such new organic magnesium phosphide or organic magnesium phosphide complex.

In other words, the present invention is summarized as follows:

[1] An organic magnesium phosphide expressed by General Formula (1):

[Chem 1]

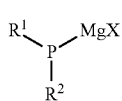

(1)

(in the formula, $R^1$ and $R^2$ are each independently an aliphatic group, heteroaliphatic group, alicyclic group, or heterocyclic group, and X is chlorine, bromine, or iodine).

[2] An organic magnesium phosphide according to [1], wherein $R^1$ and $R^2$ are tertiary alkyl groups.

[3] An organic magnesium phosphide according to [1] or [2], expressed by Formula (2) below:

[Chem 2]

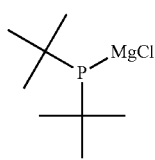

(2)

[4] An organic magnesium phosphide according to [1], wherein $R^1$ and $R^2$ are alicyclic groups.

[5] An organic magnesium phosphide according to [1] or [4], expressed by Formula (3) below:

[Chem 3]

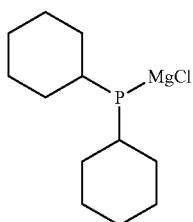

(3)

[6] A manufacturing method of an organic magnesium phosphide expressed by General Formula (4):

[Chem 4]

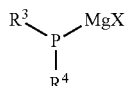

(4)

(in the formula, $R^3$ and $R^4$ are each independently an aliphatic group, heteroaliphatic group, aromatic group, alicyclic group, or heterocyclic group, and X is chlorine, bromine, or iodine); wherein such manufacturing method of organic magnesium phosphide is characterized in that the organic magnesium phosphide is prepared from: a phosphine expressed by General Formula (5):

[Chem 5]

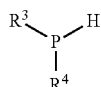

(5)

(in the formula, $R^3$ and $R^4$ are each independently an aliphatic group, heteroaliphatic group, aromatic group, alicyclic group, or heterocyclic group); and a Grignard reagent expressed by General Formula (6):

[Chem 6]

$$R^5-MgX \quad (6)$$

(in the formula, $R^5$ is an aliphatic group, heteroaliphatic group, aromatic group, alicyclic group, or heterocyclic group, and X is chlorine, bromine, or iodine).

[7] A manufacturing method of an organic magnesium phosphide expressed by General Formula (7):

[Chem 7]

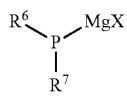

(7)

(in the formula, $R^6$ and $R^7$ are each independently an aliphatic group other than primary alkyl group or secondary alkyl group, heteroaliphatic group, alicyclic group, or heterocyclic group, and X is chlorine, bromine, or iodine); wherein such manufacturing method of organic magnesium phosphide is characterized in that the organic magnesium phosphide is prepared from: a phosphinous halide expressed by General Formula (8):

[Chem 8]

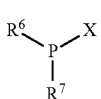
(8)

(in the formula, $R^6$ and $R^7$ are each independently an aliphatic group other than primary alkyl group or secondary alkyl group, heteroaliphatic group, alicyclic group, or heterocyclic group, and X is chlorine, bromine, or iodine); and metal magnesium.

[8] An organic magnesium phosphide complex expressed by General Formula (9):

[Chem 9]

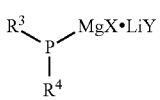
(9)

(in the formula, $R^3$ and $R^4$ are each independently an aliphatic group, heteroaliphatic group, aromatic group, alicyclic group, or heterocyclic group, and X and Y are each independently chlorine, bromine, or iodine).

[9] An organic magnesium phosphide complex according to [8], wherein $R^3$ and $R^4$ are tertiary alkyl groups.

[10] An organic magnesium phosphide complex according to [8] or [9], expressed by Formula (10) below:

[Chem 10]

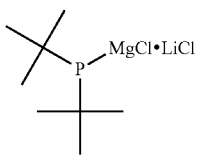
(10)

[11] An organic magnesium phosphide complex according to [8], wherein $R^3$ and $R^4$ are alicyclic groups.

[12] An organic magnesium phosphide complex according to [8] or [11], expressed by Formula (11) below:

[Chem 11]

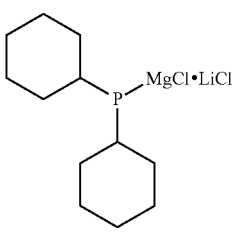
(11)

[13] A manufacturing method of an organic magnesium phosphide complex expressed by General Formula (9):

[Chem 12]

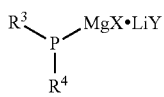
(9)

(in the formula, $R^3$ and $R^4$ are each independently an aliphatic group, heteroaliphatic group, aromatic group, alicyclic group, or heterocyclic group, and X and Y are each independently chlorine, bromine, or iodine); wherein such manufacturing method of organic magnesium phosphide complex is characterized in that the organic magnesium phosphide complex is prepared from: a phosphine expressed by General Formula (5):

[Chem 13]

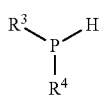
(5)

(in the formula, $R^3$ and $R^4$ are each independently an aliphatic group, heteroaliphatic group, aromatic group, alicyclic group, or heterocyclic group); and an organic magnesium complex expressed by General Formula (12):

[Chem 14]

(12)

(in the formula, $R^5$ is an aliphatic group, heteroaliphatic group, aromatic group, alicyclic group, or heterocyclic group, and X and Y are each independently chlorine, bromine, or iodine).

[14] A manufacturing method of an organic magnesium phosphide complex expressed by General Formula (13):

[Chem 15]

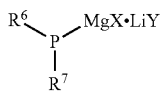
(13)

(in the formula, $R^6$ and $R^7$ are each independently an aliphatic group other than primary alkyl group or secondary alkyl group, heteroaliphatic group, alicyclic group, or heterocyclic group, and X and Y are each independently chlorine, bromine, or iodine); wherein such manufacturing method of organic magnesium phosphide complex is characterized in that the organic magnesium phosphide complex is prepared from: a phosphinous halide expressed by General Formula (8):

[Chem 16]

(8)

(in the formula, $R^6$ and $R^7$ are each independently an aliphatic group other than primary alkyl group or secondary alkyl group, heteroaliphatic group, alicyclic group, or heterocyclic group, and X is chlorine, bromine, or iodine); and metal magnesium, along with a lithium halide.

[15] A manufacturing method of organic phosphorus compound, characterized in that: an organic magnesium phosphide expressed by General Formula (4):

[Chem 17]

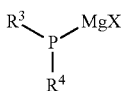
(4)

(in the formula, $R^3$ and $R^4$ are each independently an aliphatic group, heteroaliphatic group, aromatic group, alicyclic group, or heterocyclic group, and X is chlorine, bromine, or iodine), or an organic magnesium phosphide complex expressed by General Formula (9):

[Chem 18]

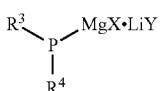
(9)

(in the formula, $R^3$ and $R^4$ are each independently an aliphatic group, heteroaliphatic group, aromatic group, alicyclic group, or heterocyclic group, and X and Y are each independently chlorine, bromine, or iodine), is reacted with an electrophile.

[16] A manufacturing method of organic phosphorus compound according to [15], characterized in that the electrophile is a compound expressed by General Formula (14), (15) or (16) below:

[Chem 19]

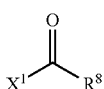
(14)

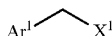
(15)

(16)

(in the formula, $R^8$ is an aliphatic group, heteroaliphatic group, aromatic group, alicyclic group, or heterocyclic group, $Ar^1$ is an aromatic group, and $X^1$ is fluorine, chlorine, bromine, iodine, or sulfonate group).

[17] A manufacturing method of organic phosphorus compound according to [15] or [16], characterized in that the electrophile is a compound expressed by General Formula (17):

[Chem 20]

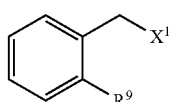
(17)

(in the formula, $R^9$ is an aliphatic group that may have been halogenated or sulfonated, or aromatic group that may have been substituted by a halogenated or sulfonated aliphatic group, and $X^1$ is fluorine, chlorine, bromine, iodine, or sulfonate group).

[18] A manufacturing method of organic phosphorus compound according to any one of [15] through [17], characterized in that: the magnesium phosphide is an organic magnesium phosphide expressed by Formula (18) below:

$$Ph_2PMgCl \quad (18);$$

and the organic magnesium phosphide complex is an organic magnesium phosphide complex expressed by Formula (19) below:

$$Ph_2PMgCl \cdot LiCl \quad (19),$$

or Formula (10) below:

[Chem 21]

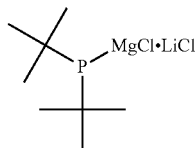
(10)

Effects of the Invention

The organic magnesium phosphide and organic magnesium phosphide complex proposed by the present invention can be prepared from magnesium which can be procured inexpensively, and is safe, in industrial applications. Use of the organic magnesium phosphide or organic magnesium phosphide complex proposed by the present invention opens the door to a new manufacturing method of organic phosphorus compound. This means that, by using the manufacturing method proposed by the present invention, a diverse range of organic phosphorus compounds can be provided for use as ligands for cross-coupling reactions using transition metal catalysts, as hardening accelerator catalysts for epoxy resins, etc., and in other fields. These possibilities make the manufacturing method proposed by the present invention useful in the manufacture of organic phosphorus compounds and very valuable in industrial applications.

MODE FOR CARRYING OUT THE INVENTION

Under the present invention, C1 to C10 alkyl groups among aliphatic groups include methyl group, ethyl group, n-propyl group, i-propyl group, n-butyl group, i-butyl group, sec-butyl group, tert-butyl group, n-pentyl group, neopentyl group, 2-pentyl group, 3-pentyl group, tert-pentyl group, n-hexyl group, i-hexyl group, 2-hexyl group, 3-hexyl group, n-heptyl group, 1-methyl hexyl group, 1-ethyl pentyl group, 2-ethyl pentyl group, 1-propyl butyl group, octyl group, nonyl group, decanyl group, 1,1-dimethyl butyl group, 1,2-dimethyl butyl group, 1,3-dimethyl butyl group, 2,2-dimethyl butyl group, 2,3-dimethyl butyl group, 3,3-dimethyl butyl group, 1-ethyl-1-methyl propyl group, 1-ethyl-2-methyl propyl group, 1,1,2-trimethyl propyl group, 1,2,2-trimethyl propyl group, 1-methyl hexyl group, 2-ethyl hexyl group, 3,7-dimethyl octyl group, and 1-methyl undecanyl group.

Also, C2 to C12 alkenyl groups include vinyl group, 1-propenyl group, isopropenyl group, allyl group, 1-butenyl group, crotyl group (2-butenyl group), 3-butenyl group, 1,3-butadienyl group, 1-pentenyl group, 2-pentenyl group, 3-pentenyl group, 4-pentenyl group, 1,3-pentadienyl group, 1,4-pentadienyl group, 2,4-pentadienyl group, 1-hexenyl group, 2-hexenyl group, 3-hexenyl group, 4-hexenyl group, 5-hexenyl group, 1,3-hexadienyl group, 1,4-hexadienyl group, 1,5-hexadienyl group, 2,4-hexadienyl group, 2,5-hexadienyl group, 3,5-hexadienyl group, 1,3,5-hexatrienyl group, 6-heptenyl group, 7-octenyl group, 9-decenyl group, 10-undecenyl group, 1-methyl vinyl group, 1-methyl propa-1-en-1-yl group, 1-methyl allyl group, 2-methyl propa-1-en-1-yl group, 2-methyl allyl group, 1-methylene propa-2-en-1-yl group, 1-methyl buta-1-en-1-yl group, 1-methyl buta-2-en-1-yl group, 1-methyl buta-3-en-1-yl group, 2-methyl buta-1-en-1 yl group, 2-methyl buta-2-en-1-yl group, 2-methyl buta-3-en-1-yl group, 3-methyl buta-1-en-1-yl group, 3-methyl buta-3-en-1-yl group, 1-methylene butyl group, 2-methylene butyl group, 1-ethyl-1-propenyl group, 1-ethyl-2-propenyl group, 1,2-dimethyl-1-propenyl group, 1,1-dimethyl-2-propenyl group, 1,2-dimethyl-2-propenyl group, 1-methylene-1-methyl propyl group, 1-methylene-2-methyl propyl group, 2-methylene-1-methyl propyl group, 2-methylene-2-methyl propyl group, 1-methylene-2-butenyl group, 1-methylene-3-butenyl group, 2-methylene-3-butenyl group, 2-methyl-2-methylene-2-propenyl group, 1-methyl-1-pentenyl group, 1-methyl-2-pentenyl group, 1-methyl-3-pentenyl group, 1-methyl-4-pentenyl group, 2-methyl-1-pentenyl group, 2-methyl-2-pentenyl group, 2-methyl-3-pentenyl group, 2-methyl-4-pentenyl group, 3-methyl-1-pentenyl group, 3-methyl-2-pentenyl group, 3-methyl-3-pentenyl group, 3-methyl-4-pentenyl group, 4-methyl-1-pentenyl group, 4-methyl-2-pentenyl group, 4-methyl-3-pentenyl group, 4-methyl-4-pentenyl group, 1-methylene pentyl group, 2-methylene pentyl group, 3-methylene pentyl group, 1-ethyl-1-butenyl group, 1-ethyl-2-butenyl group, 1-ethyl-3-butenyl group, 2-ethyl-1-butenyl group, 2-ethyl-2-butenyl group, 2-ethyl-3-butenyl group, 1-ethylidene butyl group, 1-vinyl butyl group, 1,2-dimethyl-1-butenyl group, 1,1-dimethyl-2-butenyl group, 1,2-dimethyl-2-butenyl group, 1,3-dimethyl-2-butenyl group, 2,3-dimethyl-2-butenyl group, 3,3-dimethyl-2-butenyl group, 1,1-dimethyl-3-butenyl group, 1,2-dimethyl-3-butenyl group, 1,3-dimethyl-3-butenyl group, 2,2-dimethyl-3-butenyl group, 2,3-dim ethyl-3-butenyl group, 1-methyl-1,3-pentadienyl group, 1-methyl-1,4-pentadienyl group, 1-methyl-2,4-pentadienyl group, 2-methyl-1,3-pentadienyl group, 2-methyl-1,4-pentadienyl group, 2-methyl-2,4-pentadienyl group, 3-methyl-1,3-pentadienyl group, 3-methyl-1,4-pentadienyl group, 3-methyl-2,4-pentadienyl group, 4-methyl-1,3-pentadienyl group, 4-methyl-1,4-pentadienyl group, 4-methyl-2,4-pentadienyl group, 1-methylene-2-pentenyl group, 1-methylene-3-pentenyl group, 1-methylene-4-pentenyl group, 2-methylene-3-pentenyl group, 2-methylene-4-pentenyl group, 3-methylene-1-pentenyl group, 3-methylene-4-pentenyl group, 1-ethyl-1,3-butadienyl group, 2-ethyl-1,3-butadienyl group, 1,2-dimethyl-1,3-butadienyl group, 1,3-dimethyl-1,3-butadienyl group, 2,3-dimethyl-1,3-butadienyl group, 1-ethylidene-2-butenyl group, 1-ethylidene-3-butenyl group, 2-ethylidene-3-butenyl group, 1-vinyl-3-butenyl group, 2-vinyl-3-butenyl group, 1-methylene-2-methyl-2-butenyl group, 1-methylene-2-methyl-3-butenyl group, 1-methylene-3-methyl-2-butenyl group, 1-methylene-3-methyl-3-butenyl group, 2-methylene-1-methyl-3-butenyl group, 2-methylene-3-methyl-3-butenyl group, 1,2-dimethylene butyl group, 1-methylene-2,4-pendadienyl group, 3-methylene-1,4-pentadienyl group, 1-vinyl-1,3-butadienyl group, 2-vinyl-1,3-butadienyl group, 1,2-dimethylene-3-butenyl group, 3, 7-dimethyl-6-octenyl group, and 3,7-dimethyl-2,6-octadienyl group.

Or, C2 to C12 alkynyl groups include ethynyl group, 1-propynyl group, propargyl group, 1-butynyl group, 2-butynyl group, 3-butynyl group, 1,1-dimethyl propa-2-yn-1-yl group, and the like.

Also, C6 to C18 aryl groups among aromatic groups include phenyl group, 2-tolyl group, 3-tolyl group, 4-tolyl group, 2-hydroxyphenyl group, 3-hydroxyphenyl group, 4-hydroxyphenyl group, 2-cyanophenyl group, 3-cyanophenyl group, 4-cyanophenyl group, 2-trifluoromethyl phenyl group, 3-trifluoromethyl phenyl group, 4-trifluoromethyl phenyl group, 2,4-dimethoxyphenyl group, 2,5-dimethoxyphenyl group, 2,4,6-trimethyl phenyl group, 2,4-dimethylphenyl group, 2,3-dimethylphenyl group, 3,4-dimethyl benzene, 3,5-dimethylphenyl group, 2-(trifluoromethoxy) phenyl group, 3-(trifluoromethoxy) phenyl group, 2-biphenyl group, 3-biphenyl group, 4-biphenyl group, 3,4-(methylene dioxy) phenyl group, naphthyl group, and the like.

Also, C3 to C18 cycloalkyl groups among alicyclic groups include cyclopropyl group, 1-methyl cyclopropyl group, 2-methyl cyclopropyl group, 1,2-dimethyl cyclopropyl group, 2,2-dimethyl cyclopropyl group, 2,3-dimethyl cyclopropyl group, 2,4-dimethyl cyclopropyl group, 3,3-dimethyl cyclopropyl group, cyclopropyl methyl group, (1-methyl cyclopropyl) methyl group, (2-methyl cyclopropyl) methyl group, 1-cyclopropyl ethyl group, 2-cyclopropyl ethyl group, (1,2-dimethyl cyclopropyl) methyl group, (2,2-dimethyl cyclopropyl) methyl group, (1-ethyl cyclopropyl) methyl group, (2-ethyl cyclopropyl) methyl group, 1-(1'-methyl cyclopropyl) ethyl group, 1-(2'-methyl cyclopropyl) ethyl group, 2-(1'-methyl cyclopropyl) ethyl group, 2-(2'-methyl cyclopropyl) ethyl group, 1-cyclopropyl propyl group, 2-cyclopropyl propyl group, 3-cycloprpoyl propyl group, 1,2,2-trimethyl cyclopropyl group, 1,2,3-trimethyl cyclopropyl group, 2,2,3-trimethyl cyclopropyl group, 1-ethyl-2-methyl cyclopropyl group, 2-ethyl-1-methyl cyclopropyl group, 2-ethyl-2-methyl cyclopropyl group, 1-propyl cyclopropyl group, 2-propyl cyclopropyl group, cyclobutyl group, 1-methyl cyclobutyl group, 2-methyl cyclobutyl group, 3-methyl cyclobutyl group, cyclobutyl methyl group, (1-methyl cyclobutyl) methyl group, (2-methyl cyclobutyl) methyl group, (3-methyl cyclobutyl) methyl group, 1-cyclobutyl ethyl group, 2-cyclobutyl ethyl group, 1,2-dimethyl cyclobutyl group, 2,2-dimethyl cyclobutyl group, 2,3-dimethyl cyclobutyl group, 3,3-dimethyl cyclobutyl group, 1-ethyl cyclobutyl group, 2-ethyl cyclobutyl group, 3-ethyl cyclobutyl group, cyclopentyl group, cyclopentyl methyl group, 1-methyl cyclopentyl group, 2-methyl cyclopentyl group, 3-methyl cyclopentyl group, cyclohexyl group, cyclohexyl methyl group, 1-methyl cyclohexyl group, 2-methyl cyclohexyl group, 4-methyl cyclohexyl group, cycloheptyl group, 2-cyclohexyl ethyl group, adamantyl group, norbonyl group, and the like.

Also, C3 to C18 cycloalkenyl groups among alicyclic groups include 1-cyclopropenyl group, 2-cyclopropenyl group, (1-cyclopropenyl) methyl group, (2-cyclopropenyl) methyl group, 1-cyclobutenyl group, 2-cyclobutenyl group, 2,3,3-trifluoro-1-cyclobutenyl group, 1-cyclopentenyl group, 2-cyclopentenyl group, 3-cyclopentenyl group, cyclohexa-2-en-1-yl group, bicyclo [2.2.1] hepta-2-en-7-yl group, bicyclo [3.2.1] octa-1-en-3-yl group, 1-phenyl vinyl group, 2-phenyl vinyl group, 3-phenyl-2-propenyl group, cinnamyl group, (3-phenyl propa-2-en-1-yl group), 2-ethoxyethylene group, and the like.

Also, heterocyclic groups include 2-furyl group, 2-pyridyl group, and the like.

Under the present invention, halogen atoms include fluorine atom, chlorine atom, bromine atom, and iodine atom, while reactive groups include sulfonate group.

[Organic Magnesium Phosphide]

The organic magnesium phosphide proposed by the present invention is a compound expressed by General Formula (1):

[Chem 22]

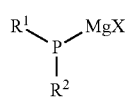

(1)

(in the formula, $R^1$ and $R^2$ are each independently an aliphatic group, heteroaliphatic group, alicyclic group, or heterocyclic group, and X is chlorine, bromine, or iodine).

In the organic magnesium phosphide expressed by General Formula (1), the aliphatic groups that may be represented by $R^1$ and $R^2$ include C1 to C10 alkyl groups, C2 to C12 alkenyl groups, or C2 to C12 alkynyl groups, where these groups may be straight-chained or branched. Among the alkyl groups, C4 to C6 are preferred, to be specific. To be more specific, isopropyl group, s-butyl group, t-butyl group, and cyclohexyl group are preferred. The most preferred are t-butyl group and cyclohexyl group. Among the alkenyl groups or alkynyl groups, C4 to C6 are preferred, to be specific. To be more specific, 1,1-dimethyl-2-propenyl group or 1,1-dimethyl-2-propynyl group is preferred.

The heteroaliphatic groups that may be represented by $R^1$ and $R^2$ include, among the aforementioned alkyl groups, alkenyl groups or alkynyl groups, those having at least one heteroatom, such as oxygen atom or nitrogen atom, either appended to their framework or as a bonded atom, where these groups may be straight-chained or branched. Among the heteroaliphatic groups, 4-tetrahydropyranyl group is preferred, to be specific.

The alicyclic groups that may be represented by $R^1$ and $R^2$ include C3 to C18 cycloalkyl groups, C3 to C18 cycloalkenyl groups, or C3 to C18 cycloalkynyl groups, which may be monocyclic or polycyclic cycloalkyl groups such as adamantyl group or norbonyl group, for example. Among the alicyclic groups, C3 to C8 cycloalkyl groups are preferred, to be specific. Specifically, cyclohexyl group is more preferred.

The heterocyclic groups that may be represented by $R^1$ and $R^2$ include alicyclic groups having at least one heteroatom in their ring structure, and aromatic groups having at least one heteroatom in their ring structure. Among the heterocyclic groups, 2-furyl group and 2-pyridyl group are preferred, to be specific.

The aforementioned substituent groups may themselves be substituted by other substituent groups; for example, an aliphatic group may be substituted by an aromatic group to form an aralkyl group, or conversely an aromatic group may be substituted by an aliphatic group to form an alkyl aryl group.

Also, the halogen represented by X is selected from a chlorine atom, bromine atom, and iodine atom, among which a chlorine atom is preferred, to be specific.

For the organic magnesium phosphide expressed by General Formula (1), preferred substituent combinations are where both $R^1$ and $R^2$ are t-butyl groups or cyclohexyl groups, and X is a chlorine atom. To be specific, it is di-t-butyl phosphanyl magnesium chloride or dicyclohexyl phosphanyl magnesium chloride.

The organic magnesium phosphide expressed by Formula (1) under the present invention was found to be manufacturable using the manufacturing method described below, and it is useful as a material (reagent) used in the manufacture of organic phosphorus compounds.

Next, representative examples of compounds included in the organic magnesium phosphide expressed by Formula (1) above under the present invention, are shown below. It should be noted, however, that the compounds included in the scope of the present invention are not limited to the following.

It should be noted that the following abbreviations used in the table refer to the corresponding groups as specified below (the same applies to Table 2): Me: Methyl group, i-Pr: Isopropyl group, Ad: Adamantyl group

TABLE 1

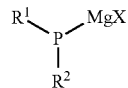

(1)

Organic Magnesium Phosphide Expressed by General Formula (1) under Present Invention

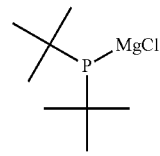

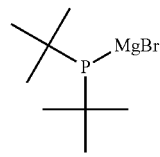

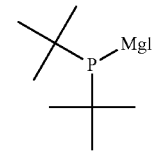

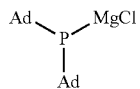

TABLE 1-continued $$\begin{array}{c} R^1\diagdown\underset{|}{P}\diagup MgX \\ R^2 \end{array} \quad (1)$$

Organic Magnesium Phosphide Expressed by General Formula (1) under Present Invention $$\begin{array}{c} Ad\diagdown\underset{|}{P}\diagup MgBr \\ Ad \end{array}$$

$$\begin{array}{c} Ad\diagdown\underset{|}{P}\diagup MgI \\ Ad \end{array}$$

[Cy₂P-MgCl structure]

[Cy₂P-MgBr structure]

[Cy₂P-MgI structure]

$$\begin{array}{c} i\text{-Pr}\diagdown\underset{|}{P}\diagup MgCl \\ i\text{-Pr} \end{array}$$

$$\begin{array}{c} i\text{-Pr}\diagdown\underset{|}{P}\diagup MgBr \\ i\text{-Pr} \end{array}$$

$$\begin{array}{c} i\text{-Pr}\diagdown\underset{|}{P}\diagup MgI \\ i\text{-Pr} \end{array}$$

(Manufacturing Method of Organic Magnesium Phosphide)

[Step a]

The organic magnesium phosphide expressed by General Formula (4) can be synthesized by reacting a phosphine expressed by General Formula (5) with a Grignard reagent expressed by General Formula (6):

[Chem 23]

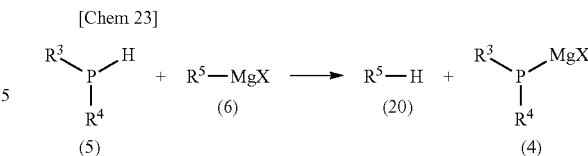

(in the formula, $R^3$ and $R^4$ are each independently an aliphatic group, heteroaliphatic group, aromatic group, alicyclic group, or heterocyclic group; $R^5$ is an aliphatic group, heteroaliphatic group, aromatic group, alicyclic group, or heterocyclic group, and X is chlorine, bromine, or iodine).

In the phosphine expressed by General Formula (5), the aliphatic groups that may be represented by $R^3$ and $R^4$ include C1 to C10 alkyl groups, C2 to C12 alkenyl groups, or C2 to C12 alkynyl groups, where these groups may be straight-chained or branched. Among the alkyl groups, C4 to C6 are preferred, to be specific. To be more specific, isopropyl group, s-butyl group, and t-butyl group are preferred. The most preferred is t-butyl group. Among the alkenyl groups or alkynyl groups, C4 to C6 are preferred, to be specific. To be more specific, 1,1-dimethyl-2-propenyl group or 1,1-dimethyl-2-propynyl group is preferred.

The heteroaliphatic groups that may be represented by $R^3$ and $R^4$ include, among the aforementioned alkyl groups, alkenyl groups, or alkynyl groups, those having at least one heteroatom, such as oxygen atom or nitrogen atom, either appended to their framework or as a bonded atom, where these groups may be straight-chained or branched. Among the heteroaliphatic groups, 4-tetrahydropyranyl group is preferred, to be specific.

The aromatic groups that may be represented by $R^3$ and $R^4$ include C6 to C18 aryl groups, which may be monocyclic or polycyclic. Among the aromatic groups, phenyl group is preferred, to be specific.

The alicyclic groups that may be represented by $R^3$ and $R^4$ include C3 to C18 cycloalkyl groups, C3 to C18 cycloalkenyl groups, or C3 to C18 cycloalkynyl groups, which may be monocyclic or polycyclic cycloalkyl groups such as adamantyl group or norbonyl group, for example. Among the alicyclic groups, C3 to C8 cycloalkyl groups are preferred, to be specific. Specifically, cyclohexyl group is more preferred.

The heterocyclic groups that may be represented by $R^3$ and $R^4$ include alicyclic groups having at least one heteroatom in their ring structure, and aromatic groups having at least one heteroatom in their ring structure. Among the heterocyclic groups, 2-furyl group and 2-pyridyl group are preferred, to be specific.

The aforementioned substituent groups may themselves be substituted by other substituent groups; for example, an aliphatic group may be substituted by an aromatic group to form an aralkyl group, or conversely an aromatic group may be substituted by an aliphatic group to form an alkyl aryl group.

Also, in the Grignard reagent expressed by General Formula (6), the substituent group represented by $R^5$ is selected from C1 to C4 aliphatic groups, where ethyl group and isopropyl group are preferred, to be specific. Also, to be more specific, chlorine atom is preferred for the halide represented by X.

It should be noted that the Grignard reagent expressed by General Formula (6) may be synthesized according to a known method, or a commercial product may be used.

The manufacturing method of the organic magnesium phosphide expressed by General Formula (4) can be implemented at a reaction temperature in a range of 0 to 60° C. The reaction temperature is more preferably in a range of 0 to 40° C., or yet more preferably in a range of 0 to 10° C.

Under the manufacturing method of the organic magnesium phosphide expressed by General Formula (4), metal salt may be added. Adding metal salt may promote the phosphide synthesis reaction in an advantageous manner. The applicable metal species include, but are not limited to, Fe, Zn, Ni, B, Al, Cu, and the like. Also, the applicable salts include, but are not limited to, fluoride, chloride, bromide, iodide, trifluoromethane sulfonate, and the like. To be more specific, $FeCl_3$ is preferred. As for the additive quantity, a feasible range is 0.1 to 10 percent by mol, or a more preferable range is 0.5 to 5 percent by mol, relative to 100 percent by mol of phosphine.

For the reaction solvents that can be used in the manufacturing method of the organic magnesium phosphide expressed by General Formula (4), tetrahydrofuran, diethyl ether, or other ether-based solvent may be used alone or mixed with benzene, toluene or other aromatic-based solvent or hexane, heptane or other hydrocarbon-based solvent, to be able to produce similar results. The use quantity of solvent is in a range of 0.1 to 10 liters, or preferably 0.3 to 2 liters, relative to 1 mol of the organic magnesium phosphide expressed by General Formula (4).

The reaction time under the manufacturing method of the organic magnesium phosphide expressed by General Formula (4) varies depending on the reaction temperature, reactant, reaction scale, etc., but it is normally in a range of 1 to 48 hours.

According to the manufacturing method of organic magnesium phosphide proposed by the present invention, the organic magnesium phosphide expressed by General Formula (4) can be manufactured without limiting the substituent groups in $R^3$ and $R^4$, compared to when a phosphinous halide is reacted with metal magnesium.

[Step b]

The organic magnesium phosphide expressed by General Formula (7) can be synthesized by reacting a dialkyl phosphinous halide expressed by General Formula (8) with metal magnesium:

[Chem 24]

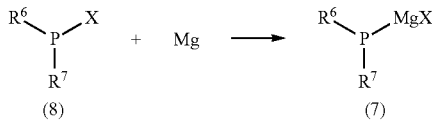

(in the formula, $R^6$ and $R^7$ are each independently an aliphatic group other than primary alkyl group or secondary alkyl group, heteroaliphatic group, alicyclic group, or heterocyclic group, and X is chlorine, bromine, or iodine).

In the dialkyl phosphinous halide expressed by General Formula (8), $R^6$ and $R^7$ are synonymous with $R^1$ and $R^2$ in Formula (1) above, except that they are not a primary alkyl group or secondary alkyl group. Primary alkyl group and secondary alkyl group are excluded from the aliphatic groups that can be $R^6$ and $R^7$ in the phosphinous halide expressed by General Formula (8), because if metal magnesium is added to the phosphinous halide expressed by General Formula (8), the organic magnesium phosphide expressed by General Formula (7) will react with the phosphinous halide expressed by General Formula (8) to prevent the synthesis.

Also, in the process of manufacturing the organic magnesium phosphide expressed by General Formula (7), the halide represented by X is selected from chlorine atom, bromine atom, and iodine atom, among which chlorine atom is preferred, to be more specific.

The manufacturing method of the organic magnesium phosphide expressed by General Formula (7) can be implemented at a reaction temperature in a range of 0 to 60° C. The reaction temperature is more preferably in a range of 30 to 60° C., or yet more preferably in a range of 50 to 60° C.

For the reaction solvents that can be used in the manufacturing method of the organic magnesium phosphide expressed by General Formula (7), tetrahydrofuran, diethyl ether or other ether-based solvent may be used alone or mixed with benzene, toluene, or other aromatic-based solvent, or hexane, heptane, or other hydrocarbon-based solvent, to be able to produce similar results. The use quantity of solvent is in a range of 0.1 to 10 liters, or preferably 0.3 to 2 liters, relative to 1 mol of the organic magnesium phosphide expressed by General Formula (7).

The reaction time under the manufacturing method of the organic magnesium phosphide expressed by General Formula (7) varies depending on the reaction temperature, reactant, reaction scale, etc., but it is normally in a range of 1 to 48 hours.

[Organic Magnesium Phosphide Complex]

The organic magnesium phosphide complex proposed by the present invention is a compound expressed by General Formula (9):

[Chem 25]

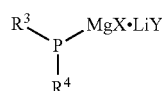

(9)

(in the formula, $R^3$ and $R^4$ are each independently an aliphatic group, heteroaliphatic group, aromatic group, alicyclic group, or heterocyclic group, and X and Y are each independently chlorine, bromine, or iodine).

In the organic magnesium phosphide complex expressed by General Formula (9), the aliphatic groups that may be represented by $R^3$ and $R^4$ include C1 to C10 alkyl groups, C2 to C12 alkenyl groups, or C2 to C12 alkynyl groups, where these groups may be straight-chained or branched. Among the alkyl groups, C4 to C6 are preferred, to be specific. To be more specific, isopropyl group, s-butyl group, and t-butyl group are preferred. The most preferred is t-butyl group. Among the alkenyl groups or alkynyl groups, C4 to C6 are preferred, to be specific. To be more specific, 1,1-dimethyl-2-propenyl group or 1,1-dimethyl-2-propynyl group is preferred.

The heteroaliphatic groups that may be represented by $R^3$ and $R^4$ include, among the aforementioned alkyl groups, alkenyl groups, or alkynyl groups, those having at least one heteroatom, such as oxygen atom or nitrogen atom, either appended to their framework or as a bonded atom, where these groups may be straight-chained or branched. Among the heteroaliphatic groups, 4-tetrahydropyranyl group is preferred, to be specific.

The aromatic groups that may be represented by $R^3$ and $R^4$ include C6 to C18 aryl groups, which may be monocyclic or polycyclic. Among the aromatic groups, phenyl group is preferred, to be specific.

The alicyclic groups that may be represented by $R^3$ and $R^4$ include C3 to C18 cycloalkyl groups, C3 to C18 cycloalkenyl groups, or C3 to C18 cycloalkynyl groups, which may be monocyclic or polycyclic cycloalkyl groups such as adamantyl group or norbonyl group, for example. Among the alicyclic groups, C3 to C8 cycloalkyl groups are preferred, to be specific. Specifically, cyclohexyl group is more preferred.

The heterocyclic groups that may be represented by $R^3$ and $R^4$ include alicyclic groups having at least one heteroatom in their ring structure, and aromatic groups having at least one heteroatom in their ring structure. Among the heterocyclic groups, 2-furyl group and 2-pyridyl group are preferred, to be specific.

The aforementioned substituent groups may themselves be substituted by other substituent groups; for example, an aliphatic group may be substituted by an aromatic group to form an aralkyl group, or conversely an aromatic group may be substituted by an aliphatic group to form an alkyl aryl group.

Also, the halogens represented by X and Y are each independently selected from chlorine atom, bromine atom and iodine atom, among which chlorine atom is preferred, to be specific.

For the organic magnesium phosphide complex expressed by General Formula (9), preferred substituent combinations are where both $R^3$ and $R^4$ are t-butyl groups, or cyclohexyl groups, or phenyl groups, and X and Y are chlorine atoms. To be specific, it is a di-t-butyl phosphanyl magnesium chloride/lithium chloride complex, or dicyclohexyl phosphanyl magnesium chloride/lithium chloride complex, or diphenyl phosphanyl magnesium chloride/lithium chloride complex.

The organic magnesium phosphide complex expressed by General Formula (9) under the present invention is useful as a material (reagent) used in the manufacture of organic phosphorus compounds where preparing a Grignard reagent or lithium reagent is difficult.

Next, representative examples of compounds included in the organic magnesium phosphide complex expressed by Formula (9) above under the present invention, are shown below. It should be noted, however, that the compounds included in the scope of the present invention are not limited to the following.

TABLE 2

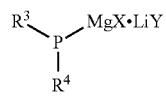
(9)

Magnesium Phosphide Complexes Expressed by General Formula (9) under Present Invention

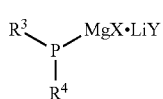

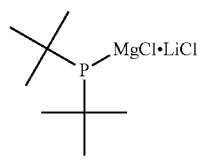

TABLE 2-continued

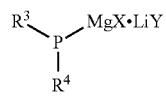
(9)

Magnesium Phosphide Complexes Expressed by General Formula (9) under Present Invention

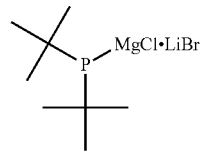

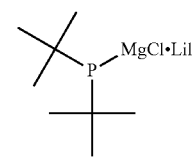

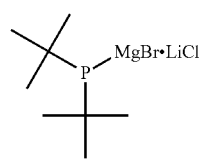

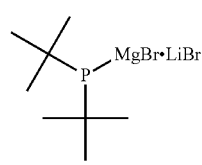

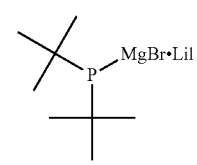

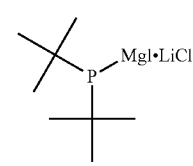

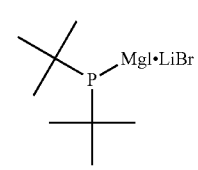

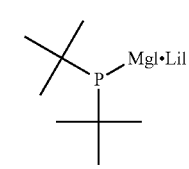

TABLE 2-continued $$\underset{R^4}{\overset{R^3}{>}}P{-}MgX\cdot LiY \quad (9)$$

Magnesium Phosphide Complexes Expressed by General Formula (9) under Present Invention Cy₂P–MgCl·LiCl Cy₂P–MgCl·LiBr Cy₂P–MgCl·LiI Cy₂P–MgBr·LiCl Cy₂P–MgBr·LiBr Cy₂P–MgBr·LiI Cy₂P–MgI·LiCl Cy₂P–MgI·LiBr Cy₂P–MgI·LiI Ph₂P–MgCl·LiCl Ph₂P–MgCl·LiBr Ph₂P–MgCl·LiI TABLE 2-continued
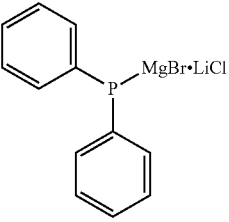 (9)
Magnesium Phosphide Complexes Expressed by General Formula (9) under Present Invention
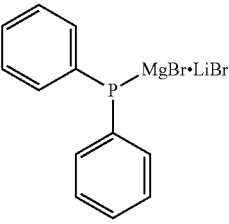
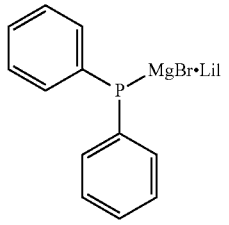
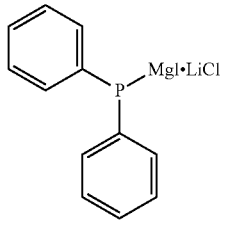
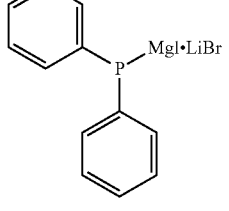
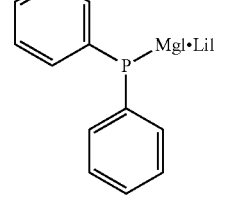
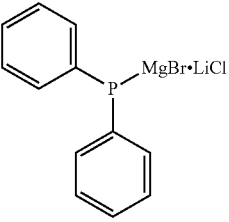
TABLE 2-continued
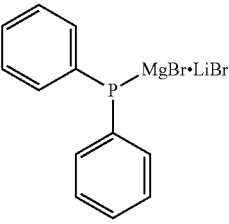 (9)
Magnesium Phosphide Complexes Expressed by General Formula (9) under Present Invention
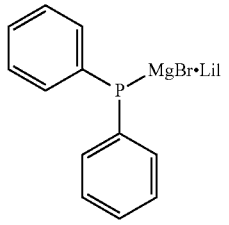
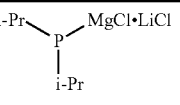
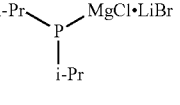
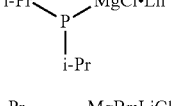
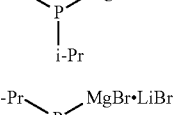
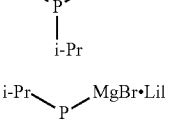
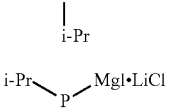
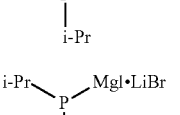
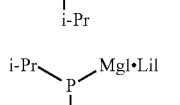
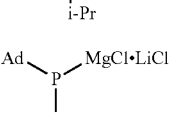
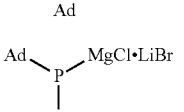
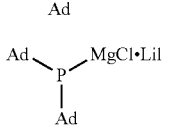
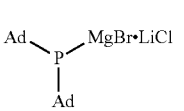
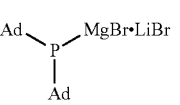

TABLE 2-continued
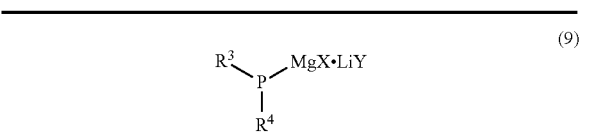
Magnesium Phosphide Complexes Expressed by General Formula (9) under Present Invention

TABLE 2-continued
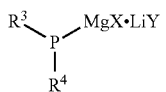
Magnesium Phosphide Complexes Expressed by General Formula (9) under Present Invention
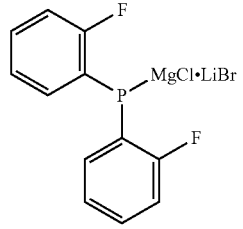
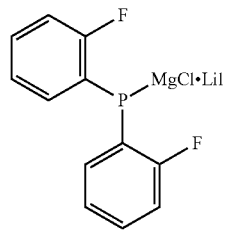
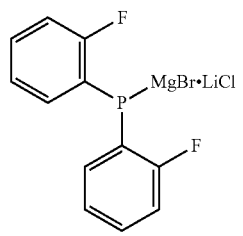
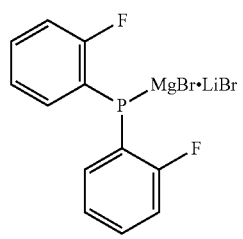
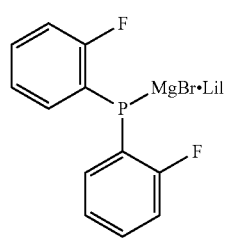
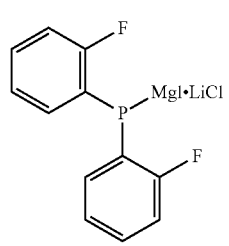
TABLE 2-continued
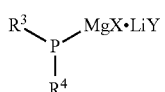
Magnesium Phosphide Complexes Expressed by General Formula (9) under Present Invention
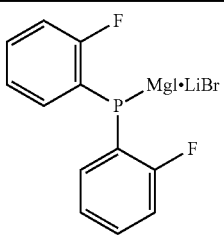
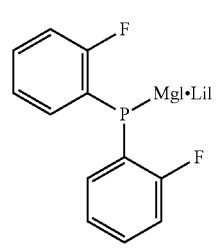
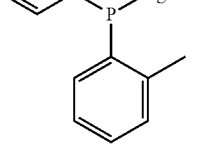
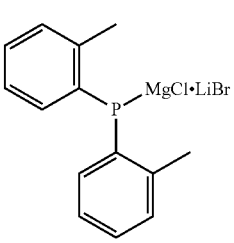
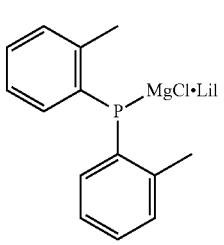
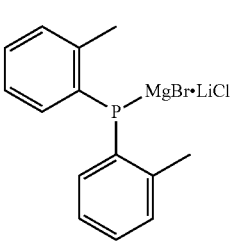

TABLE 2-continued
$$\underset{R^4}{\overset{R^3}{>}}P\text{—MgX·LiY} \quad (9)$$
Magnesium Phosphide Complexes Expressed by General Formula (9) under Present Invention
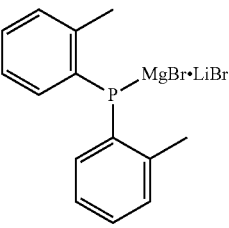
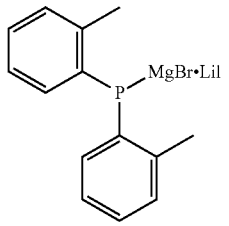
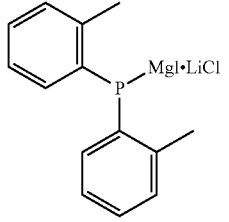
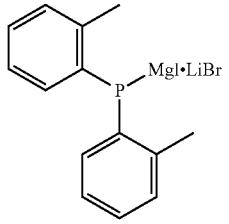
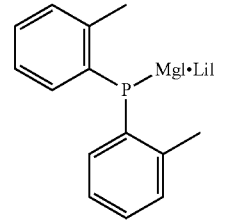
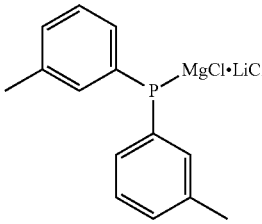
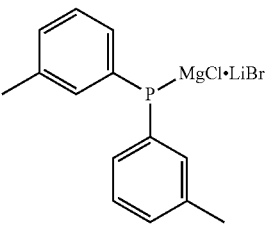
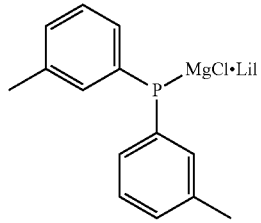
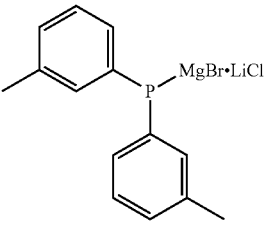
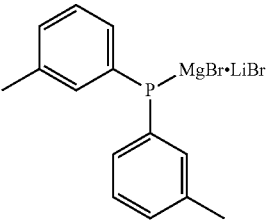
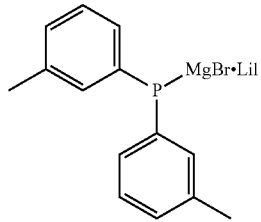
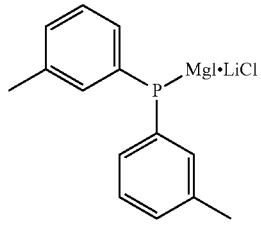

TABLE 2-continued
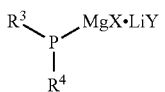
(9)
Magnesium Phosphide Complexes Expressed by General Formula (9) under Present Invention
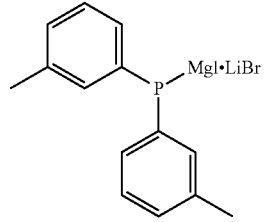
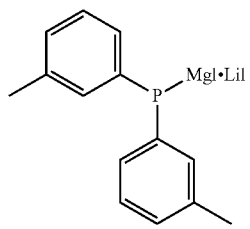
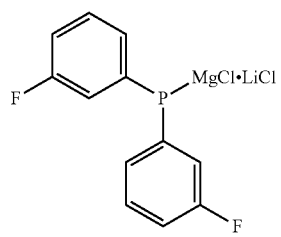
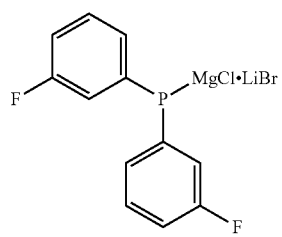
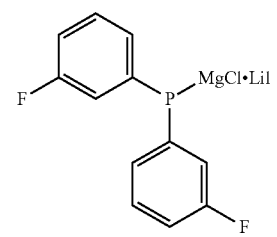
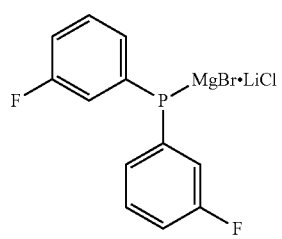
TABLE 2-continued
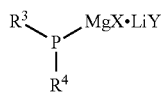
(9)
Magnesium Phosphide Complexes Expressed by General Formula (9) under Present Invention
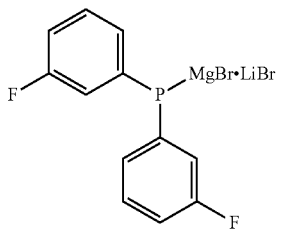
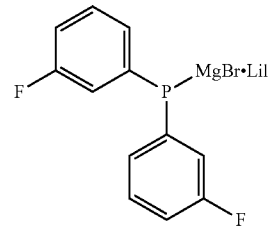
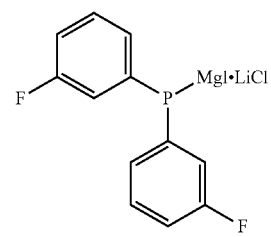
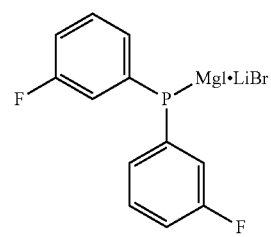
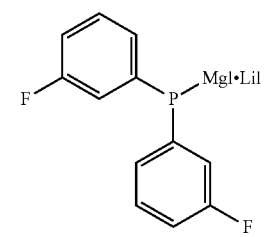
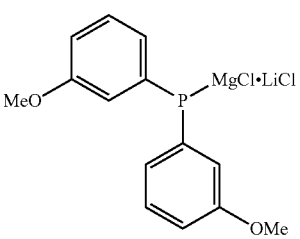

TABLE 2-continued
$$R^3\underset{R^4}{\overset{}{P}}MgX\cdot LiY \quad (9)$$
Magnesium Phosphide Complexes Expressed by General Formula (9) under Present Invention
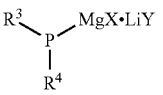
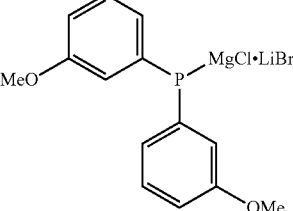
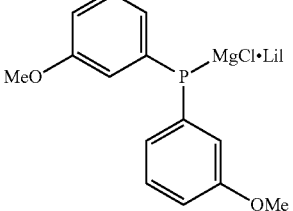
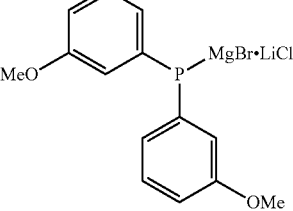
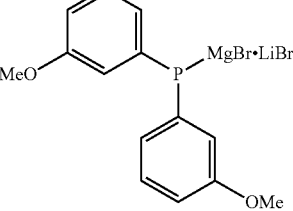
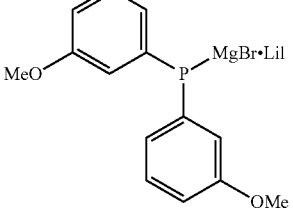
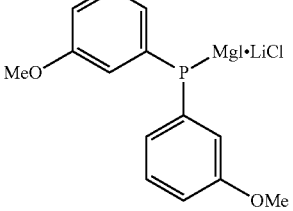
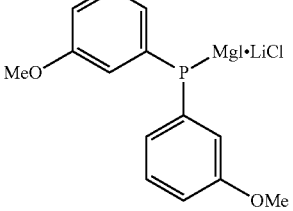
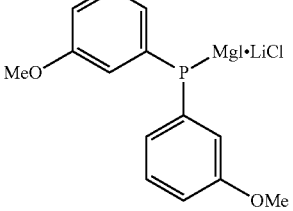
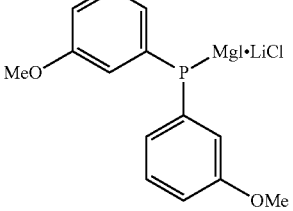
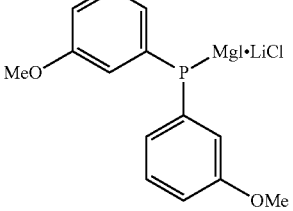
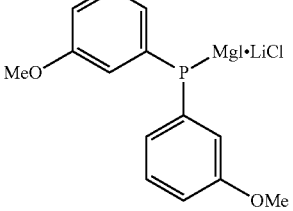
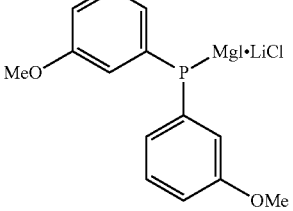
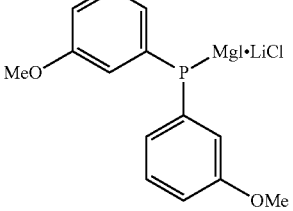

TABLE 2-continued
$$R^3\!-\!\underset{R^4}{\overset{}{P}}\!-\!MgX\cdot LiY \qquad (9)$$
Magnesium Phosphide Complexes Expressed by General Formula (9) under Present Invention
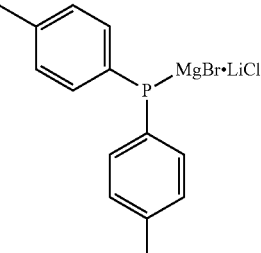
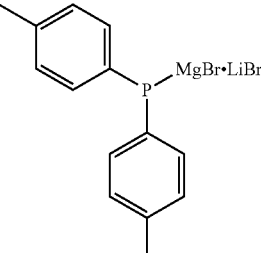
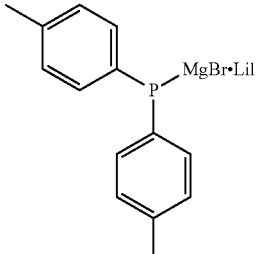
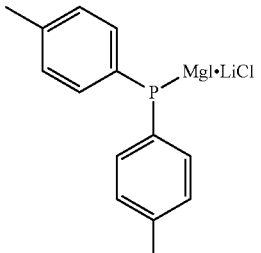
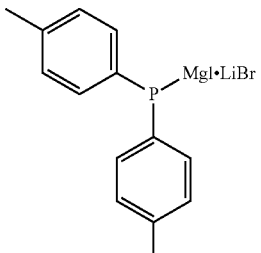
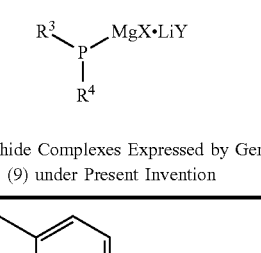
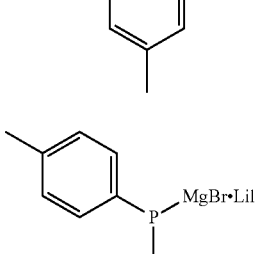
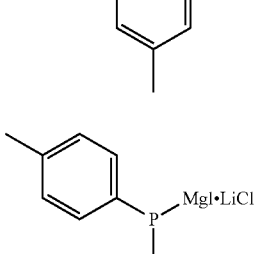
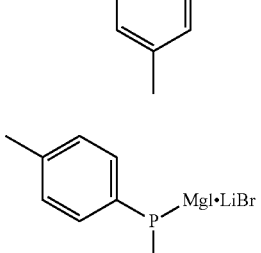
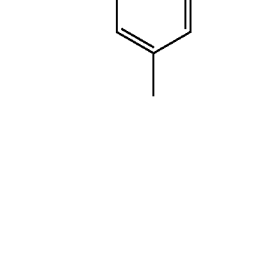

TABLE 2-continued
$$\underset{R^4}{\overset{R^3}{\diagdown}}P\text{—}MgX\cdot LiY \qquad (9)$$
Magnesium Phosphide Complexes Expressed by General Formula (9) under Present Invention
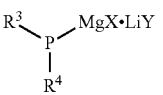
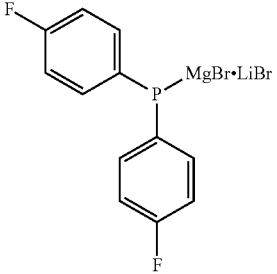
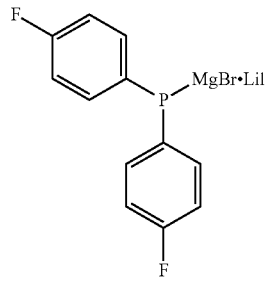
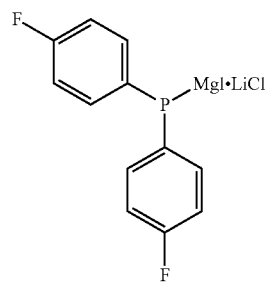
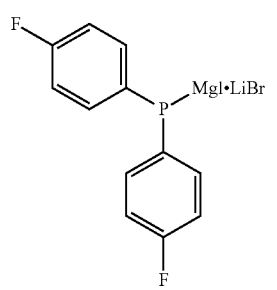
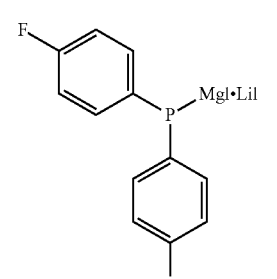

TABLE 2-continued $$\underset{R^4}{\overset{R^3}{>}}P\text{—MgX·LiY} \quad (9)$$

Magnesium Phosphide Complexes Expressed by General Formula (9) under Present Invention (4-MeO-C₆H₄)₂P–MgBr·LiI (4-MeO-C₆H₄)₂P–MgI·LiCl (4-MeO-C₆H₄)₂P–MgI·LiBr (4-MeO-C₆H₄)₂P–MgI·LiI (2-pyridyl)₂P–MgCl·LiCl (2-pyridyl)₂P–MgCl·LiBr (2-pyridyl)₂P–MgCl·LiI (2-pyridyl)₂P–MgBr·LiCl (2-pyridyl)₂P–MgBr·LiBr (2-pyridyl)₂P–MgBr·LiI (2-pyridyl)₂P–MgI·LiCl TABLE 2-continued

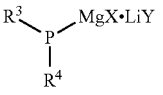

Magnesium Phosphide Complexes Expressed by General Formula (9) under Present Invention

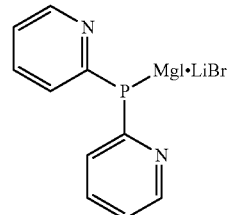

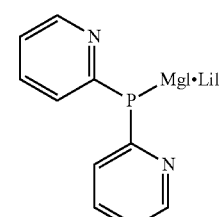

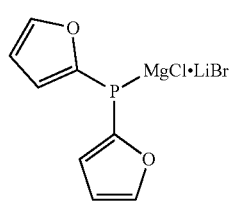

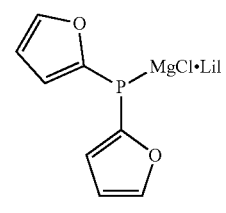

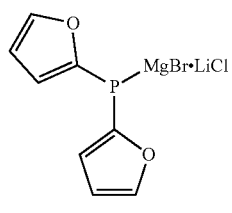

TABLE 2-continued

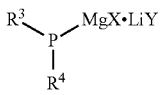

Magnesium Phosphide Complexes Expressed by General Formula (9) under Present Invention

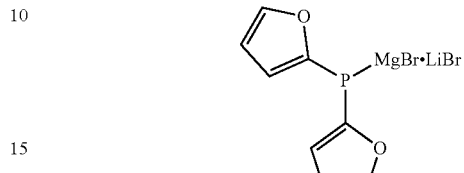

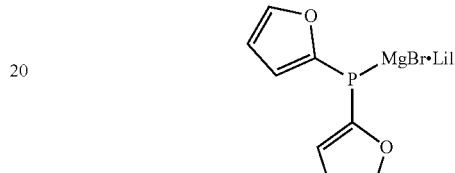

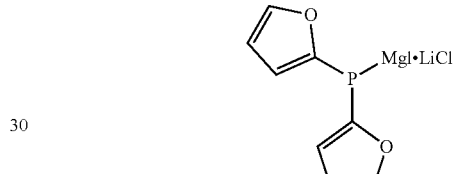

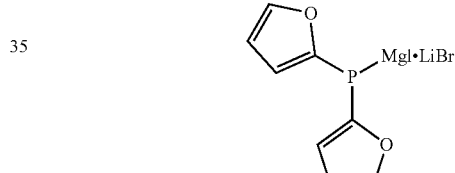

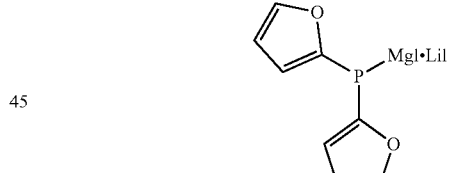

(Manufacturing Method of Organic Magnesium Phosphide Complex)

[Step A]

The organic magnesium phosphide complex expressed by General Formula (9) under the present invention can be synthesized by reacting a phosphine expressed by General Formula (5) with an organic magnesium complex expressed by General Formula (12):

[Chem 26]

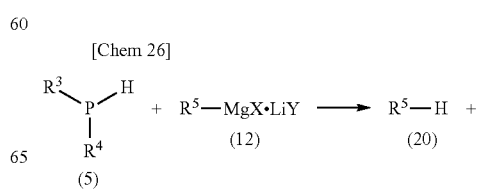

-continued

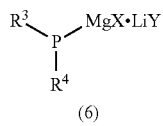

(6)

($R^3$, $R^4$, $R^5$, X, and Y are the same as above).

In the phosphine expressed by General Formula (5), $R^3$ and $R^4$ are each independently an aliphatic group, heteroaliphatic group, aromatic group, alicyclic group, or heterocyclic group, being synonymous with the corresponding symbols in the case of Formula (9) above.

Also, in the organic magnesium complex expressed by General Formula (12), the substituent groups represented by $R^5$ include aliphatic group, heteroaliphatic group, aromatic group, alicyclic group, and heterocyclic group; however, any desired substituent group may be used so long as it is exchanged with the hydrogen element in the phosphine expressed by General Formula (5). To be more specific, C1 to C4 aliphatic groups, 2,2,6,6-tetramethyl piperidyl group, and di-t-butyl phosphino group are preferred.

Also, in the process of manufacturing the organic magnesium phosphide complex expressed by General Formula (9), the halides represented by X and Y are each independently selected from chlorine atom, bromine atom, and iodine atom, among which chlorine atom is preferred for both, to be specific.

It should be noted that the phosphine expressed by General Formula (5), and the organic magnesium complex expressed by General Formula (12), may be synthesized according to a known method, or a commercial product may be used.

The manufacturing method of the organic magnesium phosphide complex expressed by General Formula (9) can be implemented at a reaction temperature in a range of 0 to 60° C. It is more preferably in a range of 0 to 40° C., or yet more preferably in a range of 0 to 10° C.

Under the manufacturing method of the organic magnesium phosphide complex expressed by General Formula (9), metal salt may be added. Adding metal salt may promote the phosphide complex synthesis reaction in an advantageous manner. The applicable metal species include, but are not limited to, Fe, Zn, Ni, B, Al, Cu, and the like. Also, the applicable salts include, but are not limited to, fluoride, chloride, bromide, iodide, trifluoromethane sulfonate, and the like. To be more specific, $FeCl_3$ is preferred. As for the additive quantity, a feasible range is 0.1 to 10 percent by mol, or a more preferable range is 0.5 to 5 percent by mol, relative to 100 percent by mol of phosphine.

For the reaction solvents that can be used in the manufacturing method of the organic magnesium phosphide complex expressed by General Formula (9), tetrahydrofuran, diethyl ether or other ether-based solvent may be used alone or mixed with benzene, toluene, or other aromatic-based solvent, or hexane, heptane, or other hydrocarbon-based solvent, to be able to produce similar results. The use quantity of solvent is in a range of 0.1 to 10 liters, or preferably 0.3 to 2 liters, relative to 1 mol of the magnesium phosphide complex expressed by General Formula (9).

The reaction time under the manufacturing method of the organic magnesium phosphide complex expressed by General Formula (9) varies depending on the reaction temperature, reactant, reaction scale, etc., but it is normally in a range of 1 to 48 hours.

[Step B]

The organic magnesium phosphide complex expressed by General Formula (13) can be synthesized by reacting a phosphinous halide expressed by General Formula (8) with metal magnesium in the presence of a lithium halide:

[Chem 27]

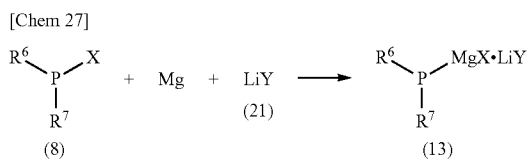

In the phosphinous halide expressed by General Formula (8), $R^6$ and $R^7$ are synonymous with $R^3$ and $R^4$ in Formula (9) above, except that they are not a primary alkyl group, secondary alkyl group, or aromatic group. Primary alkyl group and secondary alkyl group are excluded from the aliphatic groups that can be $R^6$ and $R^7$ in the phosphinous halide expressed by General Formula (8), because if metal magnesium is added to the phosphinous halide expressed by General Formula (8), the organic magnesium phosphide complex expressed by General Formula (13) will react with the phosphinous halide expressed by General Formula (8) to prevent the synthesis.

Also, in the process of manufacturing the organic magnesium phosphide complex expressed by General Formula (13), the halides represented by X and Y are each independently selected from chlorine atom, bromine atom, and iodine atom, among which chlorine atom is preferred, to be specific.

It should be noted that the phosphinous halide expressed by General Formula (8) and lithium halide may be synthesized according to a known method, or a commercial product may be used.

The manufacturing method of the magnesium phosphide complex expressed by General Formula (13) can be implemented at a reaction temperature in a range of 0 to 60° C. The reaction temperature is more preferably in a range of 0 to 40° C., or yet more preferably in a range of 0 to 10° C.

For the reaction solvents that can be used in the manufacturing method of the organic magnesium phosphide complex expressed by General Formula (13), tetrahydrofuran, diethyl ether, or other ether-based solvent may be used alone or mixed with benzene, toluene or other aromatic-based solvent or hexane, heptane, or other hydrocarbon-based solvent, to be able to produce similar results. The use quantity of solvent is in a range of 0.1 to 10 liters, or preferably 0.3 to 2 liters, relative to 1 mol of the magnesium phosphide complex expressed by General Formula (13).

The reaction time under the manufacturing method of the organic magnesium phosphide complex expressed by General Formula (13) varies depending on the reaction temperature, reactant, reaction scale, etc., but it is normally in a range of 1 to 48 hours.

When causing the reaction between the phosphinous halide and the metal magnesium, the lithium halide may be added at any time; however, preferably adding before mixing, i.e., it is added before the reaction in terms of reaction efficiency.

Under the present invention, adding a lithium halide is very effective, in particular. This is because when the organic magnesium phosphide complex expressed by Formula (13) is synthesized, the reaction liquid is obtained as a solution that permits easy manipulation, and the reaction also progresses very efficiently even at low temperatures of 5 to 10° C.

[Step C]

The organic magnesium phosphide complex expressed by General Formula (9) can also be synthesized by adding a lithium halide to an organic magnesium phosphide expressed by General Formula (4):

[Chem 28]

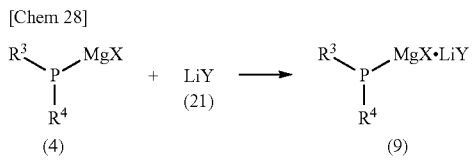

($R^3$, $R^4$, X and Y are the same as above).

As described above, the organic magnesium phosphide complex expressed by General Formula (9) can also be manufactured by adding a lithium halide to an organic magnesium phosphide expressed by General Formula (4) above.

The halogen for the lithium halide to be added to the organic magnesium phosphide expressed by General Formula (4) is selected from chlorine atom, bromine atom, and iodine atom, and to be more specific, use of lithium chloride is preferred.

Also, regarding the conditions (reaction temperature, organic solvent, reaction time, etc.), in Step C, for manufacturing the organic magnesium phosphide complex expressed by General Formula (9), those in Step B can be followed.

As described above, the magnesium phosphide complex proposed by the present invention can be manufactured by three different methods, which means that any of these methods may be selected as deemed appropriate according to the purpose of use of the complex.

(Manufacturing Method of Organic Phosphorus Compound)

The organic magnesium phosphide and organic magnesium phosphide complex proposed by the present invention can be reacted with an electrophile to be used in the synthesis of organic phosphorus compounds. The electrophile to be reacted with the organic magnesium phosphide and organic magnesium phosphide complex proposed by the present invention is not limited in any way, but preferred examples include, among others, acid halides, benzyl halide compounds, and halogen compounds expressed by General Formulas (14) through (16) below:

[Chem 29]

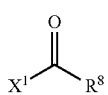

(14)

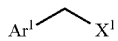

(15)

(16)

(in the formula, $R^8$ is an aliphatic group, heteroaliphatic group, aromatic group, alicyclic group, or heterocyclic group, $Ar^1$ is an aromatic group, and $X^1$ is fluorine, chlorine, bromine, iodine, or sulfonate group).

In the compounds expressed by General Formulas (14) through (16), $X^1$ is selected from fluorine, chlorine, bromine, iodine, and sulfonate group.

Also, the aliphatic groups that may be represented by $R^8$ in the acid halide expressed by General Formula (14) include C1 to C10 alkyl groups, C2 to C12 alkenyl groups, or C2 to C12 alkynyl groups, where these groups may be straight-chained or branched. The heteroaliphatic groups that may be represented by $R^8$ include, among the aforementioned alkyl groups, alkenyl groups, or alkynyl groups, those having at least one heteroatom, such as oxygen atom or nitrogen atom, either appended to their framework or as a bonded atom, where these groups may be straight-chained or branched. The aromatic groups that may be represented by $R^8$ include C6 to C18 aryl groups, which may be monocyclic or polycyclic and may contain at least one heteroatom in their ring structure. The alicyclic groups that may be represented by $R^8$ include C3 to C18 cycloalkyl groups, C3 to C18 cycloalkenyl groups, or C3 to C18 cycloalkynyl groups, which may be monocyclic or polycyclic cycloalkyl groups such as adamantyl group or norbonyl group, for example. The heterocyclic groups that may be represented by $R^8$ include alicyclic groups having at least one heteroatom in their ring structure, and aromatic groups having at least one heteroatom in their ring structure.

The aforementioned substituent groups may themselves be substituted by other substituent groups; for example, an aliphatic group may be substituted by an aromatic group to form an aralkyl group, or conversely an aromatic group may be substituted by an aliphatic group to form an alkyl aryl group.

To be more specific, the acid halides expressed by General Formula (14) include, but are not limited to, acetyl chloride and benzoyl chloride.

The aromatic groups that may be represented by $Ar^1$ in the benzyl halide compound expressed by General Formula (15) include C6 to C18 aryl groups, which may be monocyclic or polycyclic biphenyl and may contain at least one heteroatom in their ring structure. Furthermore, these groups may themselves be substituted by other substituent groups to form alkyl aryl groups.

The benzyl halide compound expressed by General Formula (15) is more preferably expressed by General Formula (17) below:

[Chem 30]

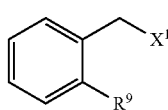

(17)

(in the formula, $R^9$ is an aliphatic group that may have been halogenated or sulfonated, or aromatic group that may have been substituted by a halogenated or sulfonated aliphatic group, and $X^1$ is fluorine, chlorine, bromine, iodine, or sulfonate group).

The aliphatic groups that may have been halogenated or sulfonated in General Formula (17) include C1 to C3 haloalkyl groups, C1 to C3 haloalkoxy groups, and C1 to C7 sulfonyloxy alkyl groups, where more preferable examples include fluoromethyl groups, chloromethyl groups, bromomethyl groups, iodomethyl groups, trifluoromethane sulfonyloxy methyl groups, and the like. Also, the aromatic groups that may have been substituted by halogenated or sulfonated aliphatic groups include phenyl groups that have been substituted by the aforementioned aliphatic groups, where more preferable examples include 2-(fluoromethyl) phenyl group, 2-(chloromethyl) phenyl group, 2-(bromomethyl) phenyl group, 2-(iodomethyl) phenyl group, 2-(trifluoromethane sulfonyloxy methyl) phenyl group, and the like.

The benzyl halide compounds expressed by General Formula (17) include, but are not limited to, benzyl chloride, α,α'-dichloro-o-xylene and 2,2'-bis (dibromometyl)-1,1-biphenyl, to be more specific.

The aliphatic groups that may be represented by $R^8$ in the halogen compounds expressed by General Formula (16) include C1 to C10 alkyl groups, C2 to C12 alkenyl groups, or C2 to C12 alkynyl groups, where these groups may be straight-chained or branched. The heteroaliphatic groups that may be represented by $R^8$ include, among the aforementioned alkyl groups, alkenyl groups, or alkynyl groups, those having at least one heteroatom, such as oxygen atom or nitrogen atom, either appended to their framework or as a bonded atom, where these groups may be straight-chained or branched. The aromatic groups that may be represented by $R^8$ include C6 to C18 aryl groups, which may be monocyclic or polycyclic and may contain at least one heteroatom in their ring structure. The alicyclic groups that may be represented by $R^8$ include C3 to C18 cycloalkyl groups, C3 to C18 cycloalkenyl groups, or C3 to C18 cycloalkynyl groups, which may be monocyclic or polycyclic cycloalkyl groups such as adamantyl group or norbornyl group, for example. The heterocyclic groups that may be represented by $R^8$ include alicyclic groups having at least one heteroatom in their ring structure, and aromatic groups having at least one heteroatom in their ring structure.

The aforementioned substituent groups may themselves be substituted by other substituent groups; for example, an aliphatic group may be substituted by an aromatic group to form an aralkyl group, or conversely an aromatic group may be substituted by an aliphatic group to form an alkyl aryl group.

The halogen compounds expressed by General Formula (16) include, but are not limited to, 1,2-dibromoethane, 2-bromo-1-chloroethane, 1,3-dibromopropane, 3-bromo-1-chloropropane, 1-bromohexane, 2-fluorobenzoic acid, 2-fluorobenzonitrile, and the like to be more specific.

It should be noted that the compounds expressed by General Formulas (14) through (16) may be synthesized according to a known method, or a commercial product may be used.

By reacting, in an organic solvent, the organic magnesium phosphide or organic magnesium phosphide complex proposed by the present invention with an acid halide, benzyl halide compound, or halogen compound serving as an electrophile, an organic phosphorus compound can be manufactured.

[Chem 31]

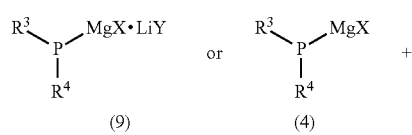

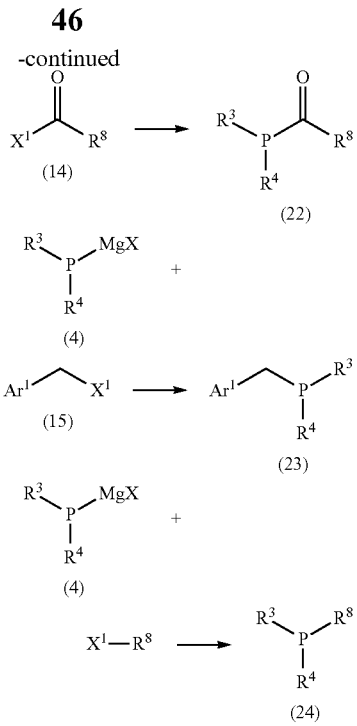

(In the formula, $R^3$, $R^4$, $R^8$, $Ar^1$, X, Y, and $X^1$ are the same as above.)

The manufacturing method of the organic phosphorus compound expressed by any one of General Formulas (22) through (24) can be implemented at a reaction temperature in a range of 0 to 60° C. The reaction temperature is more preferably in a range of 0 to 40° C., or yet more preferably in a range of 0 to 10° C.

For the reaction solvents that can be used in the manufacturing method of the organic phosphorus compound expressed by any one of General Formulas (22) through (24), tetrahydrofuran, diethyl ether or other ether-based solvent may be used alone or mixed with benzene, toluene, or other aromatic-based solvent, or hexane, heptane, or other hydrocarbon-based solvent, to be able to produce similar results. The use quantity of solvent is in a range of 0.1 to 10 liters, or preferably 0.3 to 2 liters, relative to 1 mol of the compound expressed by any one of General Formulas (14) through (16).

The reaction time under the manufacturing method of the organic phosphorus compound expressed by any one of General Formulas (22) through (24) varies depending on the reaction temperature, reactant, reaction scale, etc., but it is normally in a range of 1 to 48 hours.

The present invention is particularly useful and valuable in implementing those reactions for which acid halides and benzyl halide compounds expressed by General Formulas (14) through (16), or dihaloethane, dihalopropane, and other Grignard reagents are difficult to prepare.

For example, a di-t-butyl phosphanyl magnesium chloride/lithium chloride complex prepared according to the method proposed by the present invention, can be reacted with α,α'-dihalo-o-xylene being an electrophile expressed by General Formula (15) above, to manufacture 1,2-bis (di-t-butyl phosphinomethyl) benzene with a high isolated yield.

Also, a diphenyl phosphanyl magnesium chloride prepared according to the method proposed by the present invention, or a diphenyl phosphanyl magnesium chloride/ lithium chloride complex proposed by the present invention, can be reacted with 2,2'-dihalogenated methyl-1,1'-biphenyl being an electrophile expressed by General Formula (15) above, to manufacture 2,2'-bisdiphenyl phosphanyl methyl-1,1'-biphenyl with a high isolated yield.

The manufacturing method of organic phosphorus compound proposed by the present invention ensures high reaction selectivity and limits the generation of byproducts, which facilitates the refining process. Also, magnesium and lithium chloride, which are used as materials under the present invention, are inexpensive and easy to handle, which gives the present invention a huge advantage in the realization of low-cost, high-yield manufacturing in industrial applications.

EXAMPLES

The present invention is explained more specifically below using examples; it should be noted, however, that the present invention is not limited to these examples.

It should be note that in the examples below, purity (%) is expressed by area percentage based on gas chromatography analysis.

Example 1

Manufacturing of Di-t-Butyl Phosphanyl Magnesium Chloride 3.65 g (0.15 mol) of metal magnesium and 5 ml of tetrahydrofuran were introduced into a four-neck flask of 200 ml in capacity that had been fully replaced with nitrogen. The mixture was activated with a small quantity of dibromoethane, after which a solution prepared from 9.03 g (0.05 mol) of di-t-butyl phosphinous chloride and 101 ml of tetrahydrofuran was dripped into the mixture over 2 hours at a constant temperature between 30° C. and 40° C. After the entire solution had been dripped, the mixture was agitated for 1 hour at a temperature between 50° C. and 60° C. When the reaction liquid was brought back to 25° C. and then analyzed by gas chromatography, the rate of inversion to di-t-butyl phosphanyl magnesium chloride was 44%.

$^{31}$P-NMR spectrum (CDCl$_3$) δ ppm: 13.8

Example 2

Manufacturing of Di-t-Butyl Phosphanyl Magnesium Chloride/Lithium Chloride Complex 3.65 g (0.15 mol) of metal magnesium, 2.12 g (0.05 mol) of lithium chloride and 5 ml of tetrahydrofuran were introduced into a four-neck flask of 200 ml in capacity that had been fully replaced with nitrogen. The mixture was activated with a small quantity of dibromoethane, after which a solution prepared from 9.03 g (0.05 mol) of di-t-butyl phosphinous chloride and 45 ml of tetrahydrofuran was dripped into the mixture over 2 hours at a constant temperature between 5° C. and 10° C. After the entire solution had been dripped, the mixture was agitated for 1 hour at a temperature between 5° C. and 10° C. When the reaction liquid was brought back to 25° C. and then analyzed by gas chromatography, the rate of inversion to di-t-butyl phosphanyl magnesium chloride/lithium chloride complex was 82%.

$^{31}$P-NMR spectrum (CDCl$_3$) δ ppm: 13.9

Example 3

Manufacturing of Dicyclohexyl Phosphanyl Magnesium Chloride 0.32 g (2 mmol) of ferric chloride and 4 ml of tetrahydrofuran were introduced into a four-neck flask of 200 ml in capacity that had been fully replaced with nitrogen. Into this mixture, 75.8 g of 1.98 mol/kg isopropyl magnesium chloride-tetrahydrofuran solution was dripped over 30 minutes at a constant temperature between 0° C. and 10° C. After the entire solution had been dripped, the mixture was agitated for 30 minutes at a temperature of 0° C. Next, a solution prepared from 19.8 g (100 mmol) of dicyclohexyl phosphane and 22 ml of tetrahydrofuran was dripped into the mixture over 30 minutes at a constant temperature between 0° C. and 10° C. After the entire solution had been dripped, the mixture was agitated for 30 minutes at room temperature. Gas chromatography analysis found the rate of inversion to magnesium dicylohexyl phosphide to be 96%.

$^{31}$P-NMR spectrum (CDCl$_3$) δ ppm: −27.4

Example 4

Manufacturing of Diphenyl Phosphanyl Magnesium Chloride 1.86 g (10 mmol) of diphenyl phosphane and 10 ml of tetrahydrofuran were introduced into a four-neck flask of 100 ml in capacity that had been fully replaced with nitrogen. Into this mixture, 5.42 g of 1.9 mol/kg isopropyl magnesium chloride-tetrahydrofuran solution was dripped over 20 minutes at a constant temperature between 0° C. and 3° C. After the entire solution had been dripped, the mixture was agitated for 4 hours at a temperature of 0° C. Gas chromatography analysis found the rate of inversion to diphenyl phosphanyl magnesium chloride to be 81%.

$^{31}$P-NMR spectrum (CDCl$_3$) δ ppm: −41.4

Example 5

Manufacturing of Diphenyl Phosphanyl Magnesium Chloride/Lithium Chloride Complex 3.72 g (20 mmol) of diphenyl phosphane and 16 ml of tetrahydrofuran were introduced into a four-neck flask of 100 ml in capacity that had been fully replaced with nitrogen. Into this mixture, 15.26 g of 1.4 mol/kg isopropyl magnesium chloride/lithium chloride-THF solution was dripped over 40 minutes at a constant temperature between 0° C. and 3° C. After the entire solution had been dripped, the mixture was agitated for 4 hours at a temperature of 0° C. Gas chromatography analysis found the rate of inversion to diphenyl phosphanyl magnesium chloride/lithium chloride complex to be 90%.

$^{31}$P-NMR spectrum (CDCl$_3$) δ ppm: −41.3

Example 6

Manufacturing of Di-t-Butyl Benzoyl Phosphine

A phosphide compound that had been prepared beforehand by adding 18.1 g (0.10 mol) of di-t-butyl phosphinous chloride, 4.3 g (0.175 mol) of metal magnesium, and 4.24 g (0.10 mol) of LiCl to 89 ml of tetrahydrofuran, was introduced into a four-neck flask of 200 ml in capacity that had been fully replaced with nitrogen. Into this mixture, a solution prepared from 14.1 g (0.10 mol) of benzoyl chloride and 16 ml of toluene was dripped over 2 hours at a constant temperature between 5° C. and 10° C. After the entire solution had been dripped, the mixture was agitated for 1 hour at a temperature between 5° C. and 10° C. The reaction liquid was brought back to 25° C., after which disappearance of benzoyl chloride was confirmed by gas chromatography. Thereafter, 62 ml of 3% aqueous sulfuric acid solution was added to the reaction liquid to separate out the organic layer which was then washed with water and dried with anhydrous sodium sulfate. Furthermore, the solvent was distilled away under reduced pressure, after which the remaining liquid was distilled and the fraction of distillate was collected under a reduced pressure of 3.0 torr (400 Pa) at 84° C., and thus 19.6 g of the target di-t-butyl benzoyl phosphine (purity: 97.0%) was obtained as an oily substance. The yield was 77%.

$^1$H-NMR spectrum (CDCl$_3$) δ ppm: 1.22 (d, J=11.4 Hz, 18H, ((CH$_3$)$_3$C)$_2$P—), 7.44 (t, J=7.6 Hz, 2H), 7.54 (t, J=7.3 Hz, 1H) 8.08-8.11 (m, 2H)

Example 7

Manufacturing of Dicyclohexyl Benzoyl Phosphine

A phosphide compound that had been prepared beforehand by adding 18.1 g (0.10 mol) of di-t-butyl phosphinous chloride, 4.3 g (0.175 mol) of metal magnesium, and 4.24 g (0.10 mol) of LiCl to 89 ml of tetrahydrofuran, was introduced into a four-neck flask of 200 ml in capacity that had been fully replaced with nitrogen. Into this mixture, a solution prepared from 14.9 g (0.075 mol) of dicyclohexyl phosphine and 17 ml of toluene was dripped over 2 hours at a constant temperature between 5° C. and 10° C. After the entire solution had been dripped, the mixture was agitated for 1 hour at a temperature between 5° C. and 10° C. Next, a solution prepared from 10.5 g (0.075 mol) of benzoyl chloride and 12 ml of toluene was dripped into the mixture over 2 hours at a constant temperature between 5° C. and 10° C. After the entire solution had been dripped, the mixture was agitated for 1 hour at a temperature between 5° C. and 10° C. The reaction liquid was brought back to 25° C., after which disappearance of dicyclohexyl phosphine was confirmed by gas chromatography. Thereafter, 62 ml of 3% aqueous sulfuric acid solution was added to the reaction liquid to separate out the organic layer which was then washed with water and dried with anhydrous sodium sulfate. Furthermore, the solvent was distilled away under reduced pressure, and then 85 ml of methanol was added. When the resulting solids were dried, 17.6 g of the target dicyclohexyl benzoyl phosphine was obtained as yellow solids (yield: 78%).

$^1$H-NMR spectrum (CDCl$_3$) δ ppm: 1.04-1.33 (m, 10H), 1.62-1.77 (m, 10H), 2.02 (tq, J=11.9 Hz, 3.2 Hz, 2H), 7.45 (t, J=7.6 Hz, 2H), 7.56 (t, J=7.3 Hz, 1H) 7.99-8.02 (m, 2H)

Melting point: 75° C.

Example 8

Manufacturing of Di-t-Butyl (3-Chloropropyl) Phosphine

A phosphide compound that had been prepared beforehand by adding 18.1 g (0.10 mol) of di-t-butyl phosphinous chloride, 4.3 g (0.175 mol) of metal magnesium, and 4.24 g (0.10 mol) of LiCl to 89 ml of tetrahydrofuran, was introduced into a four-neck flask of 200 ml in capacity that had been fully replaced with nitrogen. Into this mixture, a solution prepared from 12.6 g (0.08 mol) of 3-bromo-1-chloropropane and 14 ml of toluene was dripped over 2 hours at a constant temperature between 5° C. and 10° C. After the entire solution had been dripped, the mixture was agitated for 1 hour at a temperature between 5° C. and 10° C. The reaction liquid was brought back to 25° C., after which disappearance of 3-bromo-1-chloropropane was confirmed by gas chromatography. Thereafter, 50 ml of 3% aqueous sulfuric acid solution was added to the reaction liquid to separate out the organic layer which was then washed with water and dried with anhydrous sodium sulfate. Furthermore, the solvent was distilled away under reduced pressure, after which the remaining liquid was distilled and the fraction of distillate was collected under a reduced pressure of 3.0 torr (400 Pa) at 92° C., and thus 6.6 g of the target di-t-butyl (3-chloropropyl) phosphine (purity: 96.0%) was obtained as an oily substance. The yield was 37%.

M/Z of mass spectrum (EI method): 222 (M+)

$^1$H-NMR spectrum (CDCl$_3$) δ ppm: 1.14(d, J=11.0 Hz, 18H, ((CH$_3$)$_3$C)$_2$P—), 1.50-1.54 (m, 2H), 1.95-2.04 (m, 2H), 3.64 (t, J=6.4 Hz, 2H, CH$_2$—Cl)

Example 9

Manufacturing of 1,2-Bis (Di-t-Butyl Phosphinomethyl) Benzene

A phosphide compound that had been prepared beforehand by adding 18.1 g (0.10 mol) of di-t-butyl phosphinous chloride, 7.9 g (0.325 mol) of metal magnesium, and 4.24 g (0.10 mol) of LiCl to 89 ml of tetrahydrofuran, was introduced into a four-neck flask of 200 ml in capacity that had been fully replaced with nitrogen. Into this mixture, a solution prepared from 6.07 g (0.035 mol) of α,α'-dichloro-o-xylene and 7 ml of tetrahydrofuran was dripped over 2 hours at a constant temperature between 5° C. and 10° C. After the entire solution had been dripped, the mixture was agitated for 1 hour at a temperature between 5° C. and 10° C. The reaction liquid was brought back to 25° C., after which disappearance of α,α'-dichloro-o-xylene was confirmed by gas chromatography. Thereafter, 56 ml of 3% aqueous sulfuric acid solution was added to the reaction liquid to separate out the organic layer which was then washed with water and dried with anhydrous sodium sulfate. Furthermore, the solvent was distilled away under reduced pressure, and then 52 ml of methanol was added. When the resulting solids were dried, 10.3 g of the target 1,2-bis (di-t-butyl phosphinomethyl) benzene was obtained as white solids. The yield was 75%.

$^1$H-NMR spectrum (CDCl$_3$) δ ppm: 1.14 (d, J=10.5 Hz, 36H, ((CH$_3$)$_3$C)$_2$P—), 3.04 (d, J=2.3 Hz, 4H, —CH$_2$—(P (C(CH$_3$)$_3$)$_2$), 7.03-7.08 (m, 2H), 7.52-7.55 (m, 2H)

Example 10

Manufacturing of Benzyl Diphenyl Phosphine 1.86 g (10 mmol) of diphenyl phosphane and 10 ml of tetrahydrofuran were introduced into a four-neck flask of 100 ml in capacity that had been fully replaced with nitrogen. Into this mixture, 5.42 g of 1.9 mol/kg isopropyl magnesium chloride-tetrahydrofuran solution was dripped over 20 minutes at a constant temperature between 0° C. and 3° C. After the entire solution had been dripped, the mixture was agitated for 4 hours at a temperature of 0° C., to manufacture a magnesium diphenyl phosphide. Into this magnesium diphenyl phosphide, a solution prepared from 0.92 g (7.2 mmol) of benzoyl chloride and 5 ml of tetrahydrofuran was dripped over 1 hour at a constant temperature between −1° C. and 0° C. After the entire solution had been dripped, the mixture was agitated for 14 hours at a temperature of 0° C. Thereafter, 8.2 g of toluene was added to the reaction liquid, after which 10 ml of 5% aqueous sulfuric acid solution was added to the reaction liquid to separate out the organic layer which was then washed with 10 g of water, 10 g of 5% sodium bicarbonate water, and 10 g of water, in this order. The solvent was distilled away from the obtained organic layer under reduced pressure and the residue was dissolved in 5 ml of methanol at 50° C., after which the solution was cooled to 0° C., and thus 1.52 g of benzyl diphenyl phosphine (purity: 98%) was obtained as white crystal. The yield was 75%.

$^1$H-NMR spectrum (CDCl$_3$) δ ppm: 3.40 (s, 2H, —CH$_2$P—), 7.01-7.20 (m, 5H), 7.28-7.45 (m, 10H)

$^{31}$P-NMR spectrum (CDCl$_3$) δ ppm: −9.16

Example 11

Manufacturing of Benzyl Diphenyl Phosphine 1.86 g (10 mmol) of diphenyl phosphane and 10 ml of tetrahydrofuran were introduced into a four-neck flask of 100 ml in capacity that had been fully replaced with nitrogen. Into this mixture, 7.63 g of 1.4 mol/kg isopropyl magnesium chloride/lithium chloride-THF solution was dripped over 30 minutes at a constant temperature between 0° C. and 2° C. After the entire solution had been dripped, the mixture was agitated for 4 hours at a temperature of 0° C., to manufacture a diphenyl phosphanyl magnesium chloride/lithium chloride complex. Into this complex, a solution prepared from 0.99 g (7.8 mmol) of benzoyl chloride and 5 ml of tetrahydrofuran was dripped over 1 hour at a constant temperature of 0° C. After the entire solution had been dripped, the mixture was agitated for 8 hours at a temperature of 0° C. Thereafter, 8.5 g of toluene was added to the reaction liquid, after which 10 ml of 5% aqueous sulfuric acid solution was added to the reaction liquid to separate out the organic layer which was then washed with 10 g of water, 10 g of 5% sodium bicarbonate water, and 10 g of water, in this order. The solvent was distilled away from the obtained organic layer under reduced pressure and the residue was dissolved in 5 ml of methanol at 50° C., after which the solution was cooled to 0° C., and thus 1.83 g of benzyl diphenyl phosphine (purity: 98%) was obtained as white crystal. The yield was 85%.

Example 12

Manufacturing of 2,2'-Bis (Diphenyl Phosphinous Methyl)-1,1'-Biphenyl 1.86 g (10 mmol) of diphenyl phosphine and 10 ml of tetrahydrofuran were introduced into a four-neck flask of 100 ml in capacity that had been fully replaced with nitrogen. Into this mixture, 5.42 g of 1.9 mol/kg isopropyl magnesium chloride-tetrahydrofuran solution was dripped over 20 minutes at a constant temperature between 0° C. and 3° C. After the entire solution had been dripped, the mixture was agitated for 4 hours at a temperature of 0° C., to manufacture a diphenyl phosphanyl magnesium chloride. Into this diphenyl phosphanyl magnesium chloride, a solution prepared from 1.25 g (3.6 mmol) of 2,2'-bis (dibromomethyl)-1,1'-biphenyl and 5 ml of tetrahydrofuran was dripped over 1 hour at a constant temperature between 0° C. and 1° C. After the entire solution had been dripped, the mixture was agitated for 10 hours at a temperature of 0° C. Thereafter, 8.2 g of toluene was added to the reaction liquid, after which 10 ml of 5% aqueous sulfuric acid solution was added to the reaction liquid to separate out the organic layer which was then washed with 10 g of water, 10 g of 5% sodium bicarbonate water, and 10 g of water, in this order. The solvent was distilled away from the obtained organic layer under reduced pressure and the residue was dissolved in 10 ml of propanol at 60° C., after which the solution was cooled to 0° C., and thus 1.70 g of 2,2'-bis (diphenyl phosphinous methyl)-1,1'-biphenyl (purity: 99%) was obtained as white crystal. The yield was 86%.

$^1$H-NMR spectrum (CDCl$_3$) δ ppm: 3.13&3.24 (ABq, J=13.2 Hz, 4H, (—CH2P—), 6.90 (dd, J=6.0&2.0 Hz, 2H), 7.00-7.04 (m, 2H), 7.06-7.13 (m, 8H), 7.18-7.33 (m, 16H)

$^{31}$P-NMR spectrum (CDCl$_3$) δ ppm: −10.44

Example 13

Manufacturing of 2,2'-Bis (Diphenyl Phosphinous Methyl)-1,1'-Biphenyl 3.72 g (20 mmol) of diphenyl phosphine and 16 ml of tetrahydrofuran were introduced into a four-neck flask of 100 ml in capacity that had been fully replaced with nitrogen. Into this mixture, 15.26 g of 1.4 mol/kg isopropyl magnesium chloride/lithium chloride-THF solution was dripped over 40 minutes at a constant temperature between 0° C. and 3° C. After the entire solution had been dripped, the mixture was agitated for 4 hours at a temperature of 0° C., to manufacture a diphenyl phosphanyl magnesium chloride/lithium chloride complex. Into this complex, a solution prepared from 2.66 g (7.8 mmol) of 2,2'-bis (dibromomethyl)-1,1'-biphenyl and 10 ml of tetrahydrofuran was dripped over 1 hour at a constant temperature between 0° C. and 1° C. After the entire solution had been dripped, the mixture was agitated for 12 hours at a temperature of 0° C. Thereafter, 17.7 g of toluene was added to the reaction liquid, after which 20 ml of 5% aqueous sulfuric acid solution was added to the reaction liquid to separate out the organic layer which was then washed with 20 g of water, 20 g of 5% sodium bicarbonate water, and 20 g of water, in this order. The solvent was distilled away from the obtained organic layer under reduced pressure and the residue was dissolved in 20 ml of propanol at 60° C., after which the solution was cooled to 0° C., and thus 3.86 g of 2,2'-bis (diphenyl phosphinous methyl)-1,1'-biphenyl (purity: 99%) was obtained as white crystal. The yield was 90%.

Example 14

Manufacturing of Di-t-Butyl Phosphinobenzoic Acid 1.68 g (0.042 mol) of potassium hydride and 12 ml of tetrahydrofuran were introduced into a four-neck flask of 300 ml in capacity that had been fully replaced with nitrogen. Into this mixture, a solution prepared from 5.32 g (0.038 mol) of o-fluorobenzoic acid and 12 ml of tetrahydrofuran was dripped over 1 hour at a constant temperature between 0° C. and 10° C. After the entire solution had been dripped, the mixture was agitated for 0.5 hours at a temperature between 0° C. and 10° C. Into this mixture, a phosphide compound that had been prepared beforehand by adding 6.88 g (0.038 mol) of di-t-butyl phosphinous chloride, 3.0 g (0.124 mol) of metal magnesium, and 1.61 g (0.038 mol) of LiCl to 34 ml of tetrahydrofuran, was dripped over 1 hour at a constant temperature between 0° C. and 10° C. After the entire solution had been dripped, the mixture was agitated for 1 hour at a temperature between 0° C. and 10° C. Thereafter, 27 ml of 10% aqueous sulfuric acid solution was added to the reaction liquid to separate out the organic layer which was then washed with water and dried with anhydrous sodium sulfate. Furthermore, the solvent was distilled away under reduced pressure and the resulting solids were dried, and thus 3.5 g of the target di-t-butyl phosphinobenzoic acid was obtained as white solids. The yield was 35%.

$^1$H-NMR spectrum (CDCl$_3$) δ ppm: 1.32 (d, J=19.7 Hz, 18H, ((CH$_3$)$_3$C)$_2$P—), 5.14 (d,J=256.9 Hz, 1H, —COOH), 7.62-7.77 (m, 3H), 8.16-8.18 (m, 1H)

Example 15

Manufacturing of Diphenyl Phosphinobenzoic Acid 1.20 g (0.050 mol) of sodium hydride, 28 ml of tetrahydrofuran, and 29 ml of toluene were introduced into a four-neck flask of 200 ml in capacity that had been fully replaced with nitrogen. Into this mixture, a solution prepared from 6.30 g (0.045 mol) of o-fluorobenzoic acid and 7 ml of tetrahydrofuran was dripped over 1 hour at a constant temperature between 15° C. and 20° C. After the entire solution had been dripped, the mixture was agitated for 0.5 hours at a temperature between 15° C. and 20° C. Into this mixture, a phosphide compound that had been prepared beforehand from 9.31 g (0.05 mol) of diphenyl phosphine and 26.3 g (0.06 mol) of 2.28 mol/kg isopropyl magnesium chloride-tetrahydrofuran solution was dripped over 2 hours at a constant temperature between 15° C. and 20° C. After the entire solution had been dripped, the mixture was agitated for 2 hours at a temperature between 15° C. and 20° C. Thereafter, 54 ml of 10% aqueous sulfuric acid solution was added to the reaction liquid to separate out the organic layer which was then washed with water and dried with anhydrous sodium sulfate. Furthermore, the solvent was distilled away under reduced pressure, after which 84 ml of methanol was added. When the resulting solids were dried, 7.98 g of the target diphenyl phosphinobenzoic acid was obtained as white solids. The yield was 52%.

$^1$H-NMR spectrum (CDCl$_3$) δ ppm:6.96 (m, 1H), 7.25-7.42 (m, 12H), 8.15 (m, 1H)

$^{31}$P-NMR spectrum (CDCl$_3$) δ ppm: −3.54

Example 16

Manufacturing of Diphenyl Phosphinobenzonitrile

A phosphide compound that had been prepared beforehand from 9.31 g (0.05 mol) of diphenyl phosphine and 26.3 g (0.06 mol) of 2.28 mol/kg isopropyl magnesium chloride-tetrahydrofuran solution was introduced into a four-neck flask of 200 ml in capacity that had been fully replaced with nitrogen. Into this mixture, a solution prepared from 5.45 g (0.045 mol) of o-fluorobenzonitrile and 43 ml of toluene was dripped over 1 hour at a constant temperature between 15° C. and 20° C. After the entire solution had been dripped, the mixture was agitated for 1 hour at a temperature between 15° C. and 20° C. Thereafter, 32 ml of 10% aqueous sulfuric acid solution was added to the reaction liquid to separate out the organic layer which was then washed with water and dried with anhydrous sodium sulfate. Furthermore, the solvent was distilled away under reduced pressure, and then 58 ml of methanol was added. When the resulting solids were dried, 4.88 g of the target diphenyl phosphinobenzonitrile was obtained as white solids. The yield was 38%.

M/Z of mass spectrum (EI method): 287 (M+)

$^1$H-NMR spectrum (CDCl$_3$) δ ppm: 7.04 (m, 1H), 7.28-7.49 (m, 12H), 7.70 (m, 1H)

$^{31}$P-NMR spectrum (CDCl$_3$) δ ppm: −7.87

Example 17

Manufacturing of Bis (Dicyclohexyl Phosphino) Propane Bis (Tetrafluoroboric Acid) Salt 0.32 g (0.002 mol) of iron (III) chloride and 4 ml of tetrahydrofuran were introduced into a four-neck flask of 300 ml in capacity that had been fully replaced with nitrogen. Into this mixture, 75.8 g (0.15 mol) of 1.98 mol/kg isopropyl magnesium chloride-tetrahydrofuran solution was dripped over 1 hour at a constant temperature between 0° C. and 10° C. After the entire solution had been dripped, the mixture was agitated for 0.5 hours at a temperature between 0° C. and 10° C. Into this mixture, a solution prepared from 19.8 g (0.10 mol) of dicyclohexyl phosphine and 22 ml of tetrahydrofuran was dripped over 1.0 hour at a constant temperature between 0° C. and 10° C., after which the mixture was agitated for 0.5 hours at a temperature between 20° C. and 30° C., to prepare a phosphide compound. Into this phosphide compound, a solution prepared from 10.1 g (0.05 mol) of 1,3-dibromopropane and 23 ml of toluene was dripped over 2 hours at a constant temperature between 0° C. and 10° C. After the entire solution had been dripped, the mixture was agitated for 1 hour at a temperature between 0° C. and 10° C. Thereafter, 56 ml of 3% aqueous sulfuric acid solution was added to the reaction liquid to separate out the organic layer which was then washed with water. Into the washed organic layer, 2.20 g (0.010 mol) of 40% aqueous fluoroboric acid solution was added, and then the mixture was agitated at 25° C. Thereafter, 30 ml of toluene was added to the obtained bottom layer, after which the mixture was agitated at 25° C. and then separated. Next, 60 ml of methylene chloride was added to the obtained bottom layer, after which the mixture was agitated at 25° C. The solvent was distilled away from the obtained organic layer under reduced pressure, and thus 12.0 g of the target bis (dicyclohexyl phosphino) propane bis (tetrafluoroboric acid) salt was obtained as white powder. The yield was 40%.

Melting point: 183 to 185° C.

$^{31}$P-NMR spectrum (CDCl$_3$) δ ppm: 22.9

Example 18

Manufacturing of 1,2-Bis (Dicyclohexyl Phosphinomethyl) Benzene 0.32 g (0.002 mol) of iron (III) chloride and 4 ml of tetrahydrofuran were introduced into a four-neck flask of 300 ml in capacity that had been fully replaced with nitrogen. Into this mixture, 101 g (0.20 mol) of 1.98 mol/kg isopropyl magnesium chloride-tetrahydrofuran solution was dripped over 1 hour at a constant temperature between 0° C. and 10° C. After the entire solution had been dripped, the mixture was agitated for 0.5 hours at a temperature between 0° C. and 10° C. Into this mixture, a solution prepared from 19.8 g (0.10 mol) of dicyclohexyl phosphine and 22 ml of tetrahydrofuran was dripped over 1.0 hour at a constant temperature between 0° C. and 10° C. After the entire solution had been dripped, the mixture was agitated for 0.5 hours at a temperature between 0° C. and 10° C., to prepare a phosphide compound. Into this phosphide compound, a solution prepared from 8.82 g (0.05 mol) of α,α'-dichloro-o-xylene and 20 ml of toluene was dripped over 2 hours at a constant temperature between 0° C. and 10° C. After the entiresolution had been dripped, the mixture was agitated for 1 hour at a temperature between 0° C. and 10° C. Thereafter, 43 ml of 5% aqueous sulfuric acid solution was added to the reaction liquid to separate out the organic layer which was then washed with water and dried with anhydrous sodium sulfate. Furthermore, the solvent was distilled away under reduced pressure, after which 91 ml of methanol was added. When the obtained solids were dried, 11.2 g of the target 1,2-bis (dicyclohexyl phosphinomethyl) benzene was obtained as white solids. The yield was 45%.

$^{31}$P-NMR spectrum (CDCl$_3$) δ ppm: −2.58

What is claimed is:

1. An organic magnesium phosphide expressed by General Formula (1):

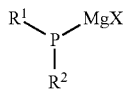
(1)

(in the formula, $R^1$ and $R^2$ are each independently an aliphatic group, heteroaliphatic group, alicyclic group, or heterocyclic group, and X is chlorine, bromine, or iodine).

2. The organic magnesium phosphide according to claim 1, wherein $R^1$ and $R^2$ are tertiary alkyl groups.

3. The organic magnesium phosphide according to claim 1, expressed by Formula (2) below:

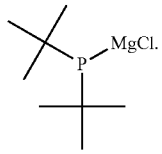
(2)

4. The organic magnesium phosphide according to claim 1, wherein $R^1$ and $R^2$ are alicyclic groups.

5. The organic magnesium phosphide according to claim 1, expressed by Formula (3) below:

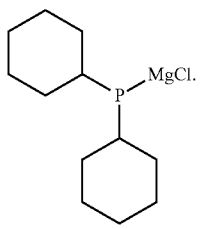
(3)

6. An organic magnesium phosphide complex expressed by General Formula (9):

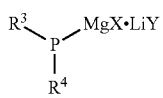
(9)

(in the formula, $R^3$ and $R^4$ are each independently an aliphatic group, heteroaliphatic group, aromatic group, alicyclic group, or heterocyclic group, and X and Y are each independently chlorine, bromine, or iodine).

7. The organic magnesium phosphide complex according to claim 6, wherein $R^3$ and $R^4$ are tertiary alkyl groups.

8. The organic magnesium phosphide complex according to claim 6, expressed by Formula (10) below:

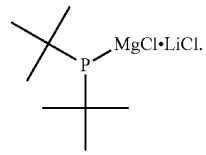
(10)

9. The organic magnesium phosphide complex according to claim 6, wherein $R^3$ and $R^4$ are alicyclic groups.

10. The organic magnesium phosphide complex according to claim 6, expressed by Formula (11) below:

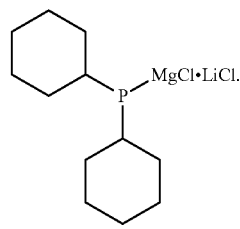
(11)

11. A manufacturing method of organic phosphorus compound, characterized in that:
an organic magnesium phosphide expressed by General Formula (4):

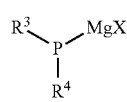
(4)

(in the formula, $R^3$ and $R^4$ are each independently an aliphatic group, heteroaliphatic group, aromatic group, alicyclic group, or heterocyclic group, and X is chlorine, bromine, or iodine), or an organic magnesium phosphide complex expressed by General Formula (9):

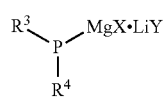
(9)

(in the formula, $R^3$ and $R^4$ are each independently an aliphatic group, heteroaliphatic group, aromatic group, alicyclic group, or heterocyclic group, and X and Y are each independently chlorine, bromine, or iodine), is reacted with an electrophile.

12. The manufacturing method of organic phosphorus compound according to claim 11, characterized in that the electrophile is a compound expressed by General Formula (14), (15) or (16) below:

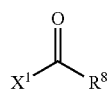
(14)

-continued

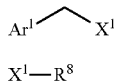
(15)

(16)

(in the formula, $R^8$ is an aliphatic group, heteroaliphatic group, aromatic group, alicyclic group, or heterocyclic group, AO is an aromatic group, and $X^1$ is fluorine, chlorine, bromine, iodine, or sulfonate group).

13. The manufacturing method of organic phosphorus compound according to claim 11, characterized in that the electrophile is a compound expressed by General Formula (17):

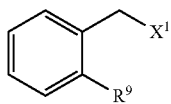
(17)

(in the formula, $R^9$ is an aliphatic group that may have been halogenated or sulfonated, or aromatic group that may have been substituted by a halogenated or sulfonated aliphatic group, and $X^1$ is fluorine, chlorine, bromine, iodine, or sulfonate group).

14. The manufacturing method of organic phosphorus compound according to claim 11, characterized in that:

the magnesium phosphide is an organic magnesium phosphide expressed by Formula (18) below:

(18); and the organic magnesium phosphide complex is an organic magnesium phosphide complex expressed by Formula (19) below:

 (19), or

Formula (10) below:

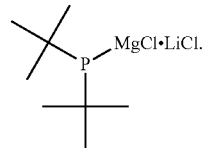
(10)

* * * * *

UNITED STATES PATENT AND TRADEMARK OFFICE
CERTIFICATE OF CORRECTION

PATENT NO. : 10,494,390 B2
APPLICATION NO. : 16/314342
DATED : December 3, 2019
INVENTOR(S) : Suzuki et al.

It is certified that error appears in the above-identified patent and that said Letters Patent is hereby corrected as shown below:

In the Claims

At Column 57, Line 9, in Claim 12, please delete "AO" and insert therefor --$Ar^1$--

At Column 58, Line 13, in Claim 14, "$Ph_2$ PMgCl.LiCl (19), or" should read --$Ph2PMgCl•LiCl$ (19), or--

Signed and Sealed this
Thirtieth Day of June, 2020

Andrei Iancu
*Director of the United States Patent and Trademark Office*